US008521441B2

(12) United States Patent
Stoughton et al.

(10) Patent No.: US 8,521,441 B2
(45) Date of Patent: *Aug. 27, 2013

(54) METHOD AND COMPUTER PROGRAM PRODUCT FOR REDUCING FLUOROPHORE-SPECIFIC BIAS

(75) Inventors: Roland Stoughton, San Diego, CA (US); Hongyue Dai, Bothell, WA (US)

(73) Assignee: Microsoft Corporation, Redmond, WA (US)

( * ) Notice: Subject to any disclaimer, the term of this patent is extended or adjusted under 35 U.S.C. 154(b) by 782 days.

This patent is subject to a terminal disclaimer.

(21) Appl. No.: 11/042,654

(22) Filed: Jan. 24, 2005

(65) Prior Publication Data

US 2005/0164273 A1    Jul. 28, 2005

Related U.S. Application Data

(60) Continuation of application No. 10/058,696, filed on Jan. 28, 2002, now abandoned, which is a division of application No. 09/222,596, filed on Dec. 28, 1998, now Pat. No. 6,351,712.

(51) Int. Cl.
*G06F 19/00* (2011.01)

(52) U.S. Cl.
USPC .......................................................... 702/20

(58) Field of Classification Search
None
See application file for complete search history.

(56) References Cited

U.S. PATENT DOCUMENTS

| | | |
|---|---|---|
| 5,155,916 A | 10/1992 | Engebretson |
| 5,510,270 A | 4/1996 | Fodor et al. |
| 5,552,270 A | 9/1996 | Khrapko et al. |
| 5,569,588 A | 10/1996 | Ashby et al. |
| 5,777,888 A | 7/1998 | Rine et al. |
| 5,800,992 A | 9/1998 | Fodor et al. |
| 5,807,522 A | 9/1998 | Brown et al. |
| 5,965,352 A | 10/1999 | Stoughton et al. |
| 6,146,830 A | 11/2000 | Friend et al. |
| 6,165,709 A | 12/2000 | Friend et al. |
| 6,171,794 B1 | 1/2001 | Burchard et al. |
| 6,203,987 B1 | 3/2001 | Friend et al. |
| 6,218,122 B1 | 4/2001 | Friend et al. |
| 6,245,517 B1 * | 6/2001 | Chen et al. .................. 506/3 |
| 6,351,712 B1 | 2/2002 | Stoughton et al. |
| 6,453,241 B1 | 9/2002 | Bassett et al. |
| 6,950,752 B1 | 9/2005 | Friend et al. |
| 7,565,251 B2 | 7/2009 | Stoughton et al. |
| 7,966,130 B2 | 6/2011 | Stoughton et al. |
| 2002/0128781 A1 | 9/2002 | Stoughton et al. |
| 2003/0093227 A1 | 5/2003 | Stoughton et al. |
| 2005/0130215 A1 | 6/2005 | Stoughton et al. |
| 2006/0190191 A1 | 8/2006 | Stoughton et al. |

FOREIGN PATENT DOCUMENTS

| | | |
|---|---|---|
| WO | WO 97/27317 A | 7/1997 |
| WO | WO 98/38329 A | 9/1998 |
| WO | WO 00/39339 | 7/2000 |

OTHER PUBLICATIONS

Shalon et al., Genome Res., 1996, vol. 6, p. 639-645.*
Lillie et al., Drug Development Research, 1997, vol. 41, p. 160-172.*
Calkins, Andrews University, www.andrews.edu/~calkins/math/webtexts/numb17.htm, Copyright 1999, p. 1-5.*
Chen et al., Journal of Medical Optics, 1997, vol. 2, No. 4, p. 364-374.*
Bogler et al., Histochemical Journal, 1993, vol. 25, p. 746-761.*
Khan et al. (Cancer Genet Cytogenet., 1998, vol. 103, p. 95-100).*
International Search Report dated Feb. 28, 2000 for PCT/US99/30837.
Blanchard et al., 1996, "Sequence to array: Probing the genome's secrets," Nature Biotechnology 14:164.
Blanchard et al., 1996, "High-Density Oligonucleotide arrays," Biosensors & Bioelectronics 11: 687-690.
Chait, 1996, "Trawling for proteins in the post-genome era," Nat. Biotech. 14:1544.
Chen et al., 1997, "Ratio-Based Decisions and the Quantitative Analysis of cDNA Microarray Images," Journal of Biomedical Optics, vol. 2, No. 4, pp. 364-374.
Ermolaeva et al., 1998, "Data management and analysis for gene expression arrays," Nature Genetics, vol. 20, pp. 19-23.
DeRisi et al., 1996, "Use of a cDNA microarray to analyze gene expression patterns in human cancer," Nature Genetics 14:457-460.
DeRisi et al., 1997, "Exploring the metabolic and genetic control of gene expression on a genomic scale," Science 278:680-686.
Lockhart et al., 1996, "Expression monitoring by hybridization to high-density oligonucleotide arrays," Nature Biotechnology 14:1675-1680.
Marton et al., 1998, "Drug target validation and identification of secondary drug target effects using DNA microarrays," Nat. Med. 4:1293-1301.
McCormack et al., 1997, "Direct analysis and identification of proteins in mixtures by LC/MS/MS and database searching at low-femtomole level," Anal. Chem. 69:767-776.
Schena et al., 1995, "Quantitative monitoring of gene expression patterns with a complementary DNA micro-array," Science 270:467-470.
Schena et al., 1996, "Parallel human genome analysis; microarray-based expression of 1000 genes," Proc. Natl. Acad. Sci. USA 93:10614-10619.
Shalon et al., 1996, "A DNA microarray system for analyzing complex DNA samples using two-color fluorescent probe hybridization," Genome Res. 6:639-645.

(Continued)

*Primary Examiner* — Pablo S Whaley
(74) *Attorney, Agent, or Firm* — Klarquist Sparkman, LLP

(57) ABSTRACT

A method for fluorophore bias removal in microarray experiments in which the fluorophores used in microarray experiment pairs are reversed. Further, a method for calculating the individual errors associated with each measurement made in nominally repeated microarray experiments. This error measurement is optionally coupled with rank based methods in order to determine a probability that a cellular constituent is up or down regulated in response to a perturbation. Finally, a method for determining the confidence in the weighted average of the expression level of a cellular constituent in nominally repeated microarray experiments.

11 Claims, 8 Drawing Sheets

(56) References Cited

OTHER PUBLICATIONS

Ruan et al., 1998, "Towards Arabidopsis Genome Analysis: Monitoring Expression Profiles of 1400 Genes Using CDNA Microarrays," Plant Journal 15:6: 821-833.
Wodikca et al, 1997, "Genome-Wide Expression Monitoring in *Saccharomyces cerevisiae*," Nature Biotechnology 15: 1359-1367.
Office Action, dated Feb. 9, 2006, for U.S. Appl. No. 10/287,130.
Office Action, dated Aug. 24, 2006, for U.S. Appl. No. 10/287,130.
Office Action, dated Apr. 17, 2007, for U.S. Appl. No. 10/287,130.
Office Action, dated Jul. 10, 2007, for U.S. Appl. No. 11/303,121.
Bevington, 1969, "Data Reduction and Error Analysis for the Physical Sciences," McGraw-Hill Inc., Chapter 5, pp. 66-91.
Bevington, 1969, "Data Reduction and Error Analysis for the Physical Sciences," McGraw-Hill Inc. Chapter 1 and Chapter 6, pp. vii-9 and 92-118.
Edwards, 1984, "An introduction to linear regression and correlation $2^{nd}$ Edition," W.H. Freeman and Company 6: pp. 65-76.
Drăghici, 2003, *Data Analysis Tools for DNA Microarrays*, Chapman & Hall/CRC Press, New York, pp. 42-55.
Lashkari et al., 1997, "Yeast microarrays for genome wide parallel genetic and gene expression analysis," Proc. Natl. Acad. Sci. USA 94, 13057-13062.
Conover et al., "Rank Transformations as a Bridge Between Parametric and Nonparametric Statistics," *The American Statistician*, vol. 35(3):124-129, 1981.
Marton et al., "Drug target validation and identification of secondary drug target effects using DNA microarrays," *Nat. Med.*, vol. 4, Nov. 1998, pp. 1293-1301.
Van Kempen et al., "Fluorescence Ratio Imaging," *Proc. First Annual Conf. of the Advanced School for Computing and Imaging*, 1995, pp. 1-10.
Werner et al., "Additive, Multiplicative, and Mixed Analytical Errors," *Clinical Chemistry*, vol. 24: No. 11, 1978, pp. 1895-1898.
Office action issued in Japanese Patent Application No. 2000-591227, which shares a priority claim with the present application, dated Jul. 7, 2009, 8 pages.
Office action issued in Japanese Patent Application No. 2000-591227, which shares a priority claim with the present application, dated Apr. 20, 2010, 3 pages (Translation Only).
Supplementary European Search Report issued in European Application No. 99967594.5, which shares a priority claim with the present application, dated Mar. 7, 2007, 8 pages.
Communication issued in European Application No. 99967594.5, which shares a priority claim with the present application, dated May 14, 2008, 6 pages.
Examination Report issued in Australian Patent Application No. 23855/00, which shares a priority claim with the present application, dated Apr. 30, 2003, 3 pages.
Examination Report issued in Canadian Patent Application No. 2,356,696, which shares a priority claim with the present application, dated Jun. 2, 2008, 4 pages.
Examination Report issued in Canadian Patent Application No. 2,356,696, which shares a priority claim with the present application, dated Apr. 6, 2009, 2 pages.
Bevington, "Data Reduction and Error Analysis for the Physical Sciences," McGraw Hill Book Company, 1969, Chapter 2.
Bevington, "Data Reduction and Error Analysis for the Physical Sciences," $2^{nd}$ Edition, McGraw Hill Book Company, 1992, Chapters, 1, 5, and 6.
Dror, "Noise Models in Gene Array Analysis," MIT Department of Electrical Engineering and Computer Science, Jun. 2001, 26 pages.
Edwards, "An Introduction to linear regression and correlation 2nd Edition," W.H. Freeman and Company, 1984, Chapters 5 and 6, pp. 49-76.
International Search Report for PCT/US99/30837, Feb. 28, 2000, 1 page.
Kim, "Statistical Methods for Estimating Doubling Time in in Vitro Cell Growth," in Vitro Cell. Dev. Biol. Animal, vol. 33, 1997, pp. 289-293.
Lee et al., "Noise Modeling and Estimation of Remotely-Sensed Images," Geoscience and Remote Sensing Symposium, $12^{th}$ Canadian Symposium on Remote Sensing International Publication Date Jul. 10-14, 1989, vol. 2, pp. 1005-1008.
Office Action, Issued in Canadian Patent Application No. 2,356,696, 4 pages, Jun. 2, 2008.
Rocke et al., "A Two-Component Model for Measurement Error in Analytical Chemistry," Technometrics, vol. 37, 1995, pp. 176-184.

\* cited by examiner

METHOD AND COMPUTER PROGRAM PRODUCT FOR REDUCING FLUOROPHORE-SPECIFIC BIAS

CROSS REFERENCE TO RELATED APPLICATION

This application is a continuation of application Ser. No. 10/058,696, filed Jan. 28, 2002, now abandoned which is a division of application Ser. No. 09/222,596, filed Dec. 28, 1998, now U.S. Pat. No. 6,351,712 B1, each of which is incorporated by reference herein in its entirety.

1 FIELD OF THE INVENTION

The field of this invention relates to methods for using data from multiple repeated experiments to generate a confidence value for each data point, increase sensitivity, and eliminate systematic experimental bias.

2 BACKGROUND OF THE INVENTION 2.1 Quantitative Measurement of Cellular Constituents There is currently an explosive increase in the generation of quantitative measurements of the levels of "cellular constituents". Cellular constituents include gene expression levels, abundance of mRNA encoding specific genes, and protein expression levels in a biological system. Levels of various constituents of a cell, such as mRNA encoding genes and/or protein expression levels, are known to change in response to drug treatments and other perturbations of the cell's biological state. Measurements of a plurality of such "cellular constituents" therefore contain a wealth of information about the affect of perturbations on the cell's biological state. The collection of such measurements is generally referred to as the "profile" of the cell's biological state.

There may be on the order of 100,000 different cellular constituents for mammalian cells. Consequently, the profile of a particular cell is typically complex. The profile of any given state of a biological system is often measured after the biological system has been subjected to a perturbation. Such perturbations include experimental or environmental conditions(s) associated with a biological system such as exposure of the system to a drug candidate, the introduction of an exogenous gene, the deletion of a gene from the system, or changes in culture conditions. Comprehensive measurements of cellular constituents, or profiles of gene and protein expression and their response to perturbations in the cell, therefore have a wide range of utility including the ability to compare and understand the effects of drugs, diagnose disease, and optimize patient drug regimens. In addition, they have further application in basic life science research.

Within the past decade, several technological advances have made it possible to accurately measure cellular constituents and therefore derive profiles. For example, new techniques provide the ability to monitor the expression level of a large number of transcripts at any one time (see, e.g., Schena et al., 1995, Quantitative monitoring of gene expression patterns with a complementary DNA micro-array, *Science* 270: 467-470; Lockhart et al., 1996, Expression monitoring by hybridization to high-density oligonucleotide arrays, *Nature Biotechnology* 14: 1675-1680; Blanchard et al., 1996, Sequence to array: Probing the genome's secrets, *Nature Biotechnology* 14, 1649; U.S. Pat. No. 5,569,588, issued Oct. 29, 1996 to Ashby et al. entitled "Methods for Drug Screening"). In organisms for which the complete genome is known, it is possible to analyze the transcripts of all genes within the cell. With other organisms, such as humans, for which there is an increasing knowledge of the genome, it is possible to simultaneously monitor large numbers of the genes within the cell.

In another front, the direct measurement of protein abundance has been improved by the use of microcolumm reversed-phase liquid chromatography electrospray ionization tandem mass spectrometry (LC/MS/MS) to directly identify proteins contained in mixtures. This technology promises to push the dynamic range for which protein abundance can be measured in a biological system. Using LC/MS/MS, McCormack et al. have demonstrated that proteins presented in system mixtures can be readily identified with a 30-fold difference in molar quantity, that the identifications are reproducible, and that proteins within the mixture can be identified at low femtomole levels. McCormack et al., 1997, Direct analysis and identification of proteins in mixtures by LC/MS/MS and database searching at the low-femtomole level, *Anal. Chem.* 69: 767-776. In a review of tandem mass spectrometry, Chait points out that an additional advantage of this technology is that it is orders of magnitude faster than more conventional approaches such as Edman sequencing. Chait, 1996, Trawling for proteins in the post-genome era, *Nat. Biotech.* 14: 1544.

Other technological advances have provided for the ability to specifically perturb biological systems with individual genetic mutations. For example, Mortensen et al. describe a method for producing embryonic stem (ES) cell lines whereby both alleles are inactivated by homologous recombination. Using the methods of Mortensen et al., it is possible to obtain homozygous mutationally altered cells, i.e., double knockouts of ES cell lines. Mortensen et al. propose that their method may be generally applicable to other genes and to cell lines other than ES cells. M Mortensen et al. 1992, Production of homozygous mutant ES cells with a single targeting construct, *Cell Biol.* 12: 2391-2395.

In another promising technology Wach et al. provide a dominant resistance module for selection of *S. cerevisiae* transformants which entirely consists of heterologous DNA. The module can also be used to provide PCR based gene disruptions. Wach et al., 1994, New heterologous modules for classical or PCR-based gene disruptions in *Saccharomyces cerevisiae*, *Yeast* 10: 1793-808.

Technological advances, such as the use of microarrays, are already being used in rug discovery (See e.g. Marton et al., 1998, Drug target validation and identification of secondary drug target effects using Microarrays, *Nature Medicine* in press; Gray et al., 1998, Exploiting chemical libraries, structure, and genomics in the search for kinase inhibitors, *Science* 281: 533-538).

Comparison of profiles with other profiles in a database (see, e.g., U.S. Pat. No. 5,777,888, issued Jul. 7, 1998 to Rine et al. entitled "Systems for generating and analyzing stimulus-response output signal matrices") or clustering of profiles by similarity can give clues to the molecular targets of drugs and related functions, efficacy and toxicity of drug candidates and/or pharmacological agents. Such comparisons may also be used to derive consensus profiles representative of ideal drug activities or disease states. Profile comparison can also help detect diseases in a patient at an early stage and provide improved clinical outcome projections for a patient diagnosed with a disease.

2.2 Fluorophore Bias

The use of two fluorophores has been described by Shalon et al., 1996, "A microarray system for analyzing complex DNA samples using two-color fluorescent probe hybridization," Genome Research 6:629-645. The problem with the approach put forth by Shalon is that each species of mRNA molecule has a bias in its measured color ratio due to interaction of the fluorescent labeling molecule with either the reverse transcription of the mRNA or with the hybridization efficiency or both. Without any error correction scheme to account for this bias, the data from a single microarray experiment, or even a plurality of nominal repeats of a microarray experiment in which the various results are averages, will produce an unacceptable error rate. As used herein, the term nominal repeat or nominally repeated experiment refers to experiments that are run under essentially the same or similar experimental conditions such that it would be useful to combine the results of the repeated experiments.

2.3 Inherent Error Rates of Cellular Constituent Quantitative Measurement Experiments While the technological advances have allowed for the generation of quantitative measurements of the levels cellular constituents, the experiments are expensive. A single microarray experiment, or a single gel electrophoresis place, can cost in the neighborhood of $100-$1000 and higher. Also, it has only become apparent after many initial attempts to apply the data to actual commercial needs that individual experiments suffer from high levels of false positives in the sense of declaring significance where there really is none. Because of the expense involved, and the high rate of false positives, no description of robust methods for repeating and statistically combining multiple, nominally identical experiments for the express purpose of data quality improvement have been provided in the prior art.

The power of genome-wide cell profiling accomplished with microarrays is in its ability to survey response to known perturbations across essentially the entire set of cellular mechanisms. However, in any given experiment, typically only a small number of cellular constituents may have dramatic changes in abundance, where the vast majority are unchanged. There are exceptions, but cells have specific, biologically fairly insulated responses to stimuli, and so most profiles involve a large set of constituents with 'no-change', and a much smaller set that are either up or down regulated. For this reason, even a small false alarm rate in the measurements can severely compromise their utility. For example, if one percent of cellular constituents actually respond in a typical experiment, the resolution in the measurement is twofold, and the errors exceed twofold one percent of the time, then there will be as many false alarms as true detections above a twofold threshold.

In general, the art has underappreciated the extensive amount of errors that are present in individual cellular constituent quantification experiments such as microarray or protein gel experiments. In addition to the difficulty posed by the fairly insulated response biological systems have to any given perturbation, a substantial amount of error is present in any nominal microarray experiment due to artifacts such as unevenly printed DNA probe spots on the microarray, scratches dust and artifacts on the microarray, unevenness in signal brightness across the microarray due to nonuniform DNA hybridization, and color stripes due fluorophore-specific biases of fluorophores used in the microarray process.

One method to reduce the effects of these serious errors is to repeat the experiment under identical conditions and to average the data. However, simple averaging of the data without any consideration of the nature of the underlying experimental errors does not provide an adequate solution to the problems the experimental errors introduce. If only simple averaging of the data is performed, an excessive number of nominal repeats would be required in order to reduce the effects of error down to an acceptable level. However, because of the expense involved in performing each cellular constituent quantification experiment, this is not a feasible solution. Accordingly, what is needed in the art are robust methods for combining the experimental results of repeated cellular constituent quantification experiments so that a minimal set of nominal repeats can provide an acceptable error rate.

Discussion of citation of a reference herein shall not be construed as an admission that such citation is prior art to the present invention.

3 SUMMARY OF THE INVENTION

This invention provides solutions for minimizing the number of times a cellular constituent quantification experiment must be repeated in order to produce data that has acceptable error levels. Accordingly, the methods of the present invention provide a novel method for fluorophore bias removal. This allows for the attenuation of fluorophore specific biases to acceptable levels based on only two nominal repeats of a cellular constituent quantification experiment. The present invention further provides methods for combining nomimal repeats of a cellular constituent quantification experiment based on rank order of up-regulation or down-regulation. In these methods, cellular constituent up- or down-regulation data determined from nominal repeats of cellular constituent quantification experiments are expressed by a novel metric that is free of intensity dependent errors. Application of this metric before combining based on rank order provides a powerful method for removing error from weakly expressing cellular constituents without an excessive number of nominal repetitions of the expensive cellular constituent quantification experiment.

Another aspect of the present invention is an improved method for computing a weighted average of individual cellular constituent measurements in nominally repeated cellular constituent quantification experiments. In particular, a novel method for calculating the error associated with each cellular constituent measurement is provided. By using this novel method for calculating error, the error bar in the weighted average is sharply attenuated. One skilled in the art will appreciate that these improved methods for computing a weighted average are applicable to two-fluorophore (two-color) or single fluorophore (one-color) protocols.

One embodiment of the present invention provides a method of fluorophore bias removal comprising the steps of:

(a) labeling a first pool of genetic matter, derived from a biological system representing a baseline state, with a first fluorophore to obtain a first pool of fluorophore-labeled genetic matter;

(b) labeling a second pool of genetic matter, derived from a biological system representing a perturbed state, with a second fluorophore to obtain a second pool of fluorophore-labeled genetic matter;

(c) labeling a third pool of genetic matter, derived from said biological system representing said baseline state, with said second fluorophore to obtain a third pool of fluorophore-labeled genetic matter;

(d) labeling a fourth pool of genetic matter, derived from said biological system representing said perturbed state, with said first fluorophore to obtain a fourth pool of fluorophore-labeled genetic matter;

(e) independently contacting said first pool of fluorophore-labeled genetic matter and said second pool of fluorophore-labeled genetic matter with a first microarray under conditions such that hybridization can occur and determining a first color ratio between said first pool of fluorophore-labeled genetic matter and said second pool of fluorophore-labeled genetic matter that binds to said microarray;

(f) independently contacting said third pool of fluorophore-labeled genetic matter and said fourth pool of fluorophore-labeled genetic matter with a second microarray under conditions such that hybridization can occur and determining a second color ratio between said third pool of fluorophore-labeled genetic matter and said fourth pool of fluorophore-labeled genetic matter; and (g) computing an average color ratio by averaging said first color ratio and said second color ratio.

Another embodiment of the invention provides a method for determining a probability that an expression level of a cellular constituent in a plurality of paired differential microarray experiments is altered by a perturbation, wherein each paired differential microarray experiment in said plurality of paired differential microarray experiments comprises a first microarray experiment representing a baseline state of a first biological system, and a second microarray experiment representing a perturbed state of said first biological system, said method comprising the steps of (a) determining an error distribution statistic by fitting a reference pair of microarray experiments with an intensity independent statistic, wherein said reference pair of microarray experiments comprises a first reference microarray experiment, and a second reference microarray experiment that is a nominal repeat of said first reference microarray experiment;

(b) selecting said cellular constituent from a set of cellular constituents measured in said plurality of paired differential microarray experiments, and, for each paired differential microarray experiment in said plurality of paired differential microarray experiments, determining an amount of change in expression level of said cellular constituent between the second microarray experiment and the first microarray experiment of said paired differential microarray experiment using said error distribution statistic; and (c) determining said probability that said expression level of said cellular constituent in said plurality of paired differential microarray experiments is altered by said perturbation by combining said amount of change in expression level of said cellular constituent determined in step (b) for each paired differential microarray experiment in said plurality of paired differential microarray experiments using a rank based method.

Yet another embodiment of the invention is a method for determining a weighted mean differential intensity in an expression level of a cellular constituent in a biological system in response to a perturbation, the method comprising:

(a) determining an error distribution statistic by fitting a reference microarray experiment pair with an intensity independent statistic, wherein the reference microarray experiment pair comprises a first reference microarray experiment and a second reference microarray experiment which is a nominal repeat of the first reference microarray experiment;

(b) determining an amount of differential expression of the cellular constituent a plurality of times;

(c) for each amount of differential expression determined in accordance with (b), calculating a corresponding amount of error based on a magnitude derived by the error distribution statistic; and (d) computing the weighted mean differential intensity by inversely weighting each amount of the differential expression of the cellular constituent determined in step (b) by the corresponding amount of error determined in step (c) according to the formula $$x = \frac{\sum (x_i / \sigma_i^2)}{\sum (1 / \sigma_i^2)}$$

where x is the weighted mean differential intensity of the cellular constituent, $x_i$ is a differential expression measurement of the cellular constituent i and $\sigma_i^2$ is a corresponding error for mean differential intensity $x_i$.

4 BRIEF DESCRIPTION OF THE FIGURES

FIG. 1 depicts some sources of measurement error present in microarray fluorescent images. Panel (a) depicts unevenly printed DNA probe spots. Panel (b) depicts the effects of scratches, dust, and artifacts. Panel (c) depicts how spot positions drift away from a nominal measuring grid. Panel (d) depicts the effects of unevenness in the brightness across the microarray due to uneven hybridization. Panel (e) depicts the effects of color stripes on the microarray due to fluorophore-specific biases.

FIG. 2 illustrates the effect of deleting genes responsible for the production of calcineurin protein in the yeast *S. Cerevisiae* (CNA1 and CNA2). The figure contrasts the response profile of two yeast cultures, a native culture (Culture 1) and a culture in which CNA1 and CNA2 have been deleted (Culture 2). The horizontal axis is the $\log_{10}$ of the intensity of the individual hybridized spots on the microarray obtained from the two yeast cultures, and therefore represents mRNA species abundance. The vertical axis is the $\log_{10}$ of the ratio of the intensity measured for one fluorescent label (Culture 1) to that measured for the other label (Culture 2) (expression ratio). True signature genes of a CNA1/CNA2 mutation are identified as those deviating significantly from the $\log_{10}$ (expression ratio)=0 line and are labeled.

FIG. 3 depicts the intensity-dependent bias that occurs in cell expression profile experiments due to variance in fluorophore optical detection efficiencies as well as variance in fluorophore incorporation efficiencies.

FIG. 4a is a color ratio vs. intensity plot for an experiment in which both cultures were the same background strain of the yeast *S. cerevisiae*. Genes with a distinct bias between a red and green fluorophore are flagged. FIG. 4b is the same experiment as depicted in FIG. 4a except that usage of the red and green fluorophores is reversed. FIG. 4c depicts the bias removal process of the invention, wherein FIG. 4a and FIG. 4b are combined to produce a response profile free of fluorophore-specific biases.

FIG. 5 compares two identical response profiles that were performed under identical experimental conditions. The figure shows that experimental errors decrease as a function of intensity (expression level). Intensity independent contour lines illustrate a component of the error correction methods of the present invention.

FIG. 6b shows the results of applying a weighted average according to the methods of the present invention to four repeats of the experiment depicted in FIG. 6a.

5 DETAILED DESCRIPTION OF THE INVENTION

5.1. Introduction and general definitions

Figure 1A:
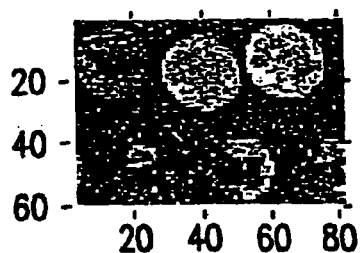
Figure 1B:
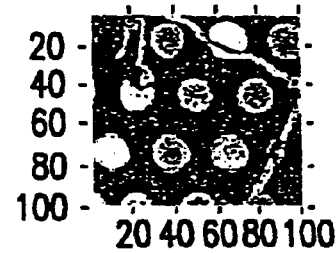
Figure 1C:
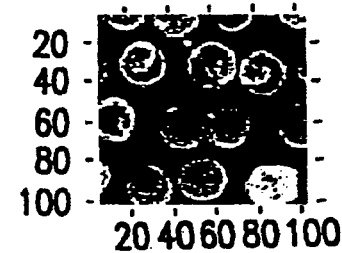
Figure 1D:
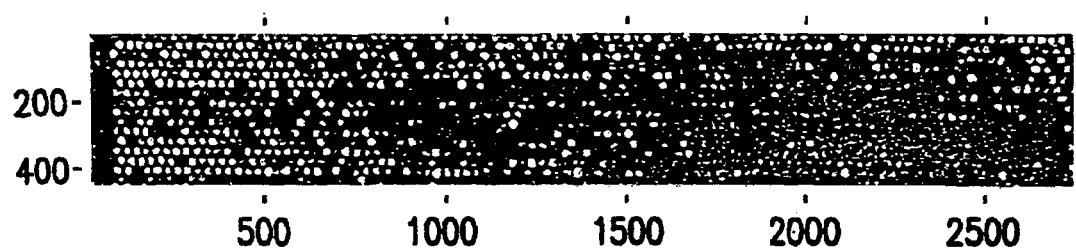
Figure 1E:
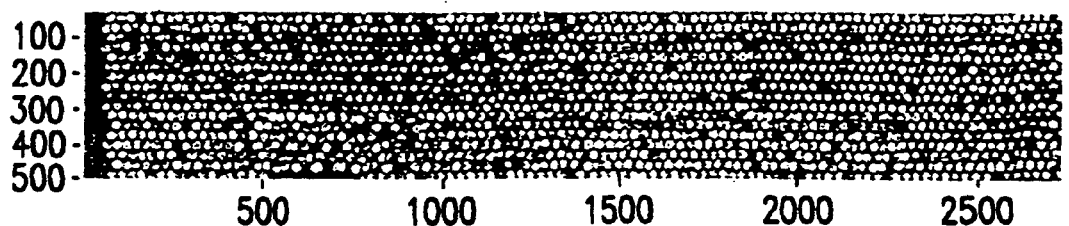
Figure 2:
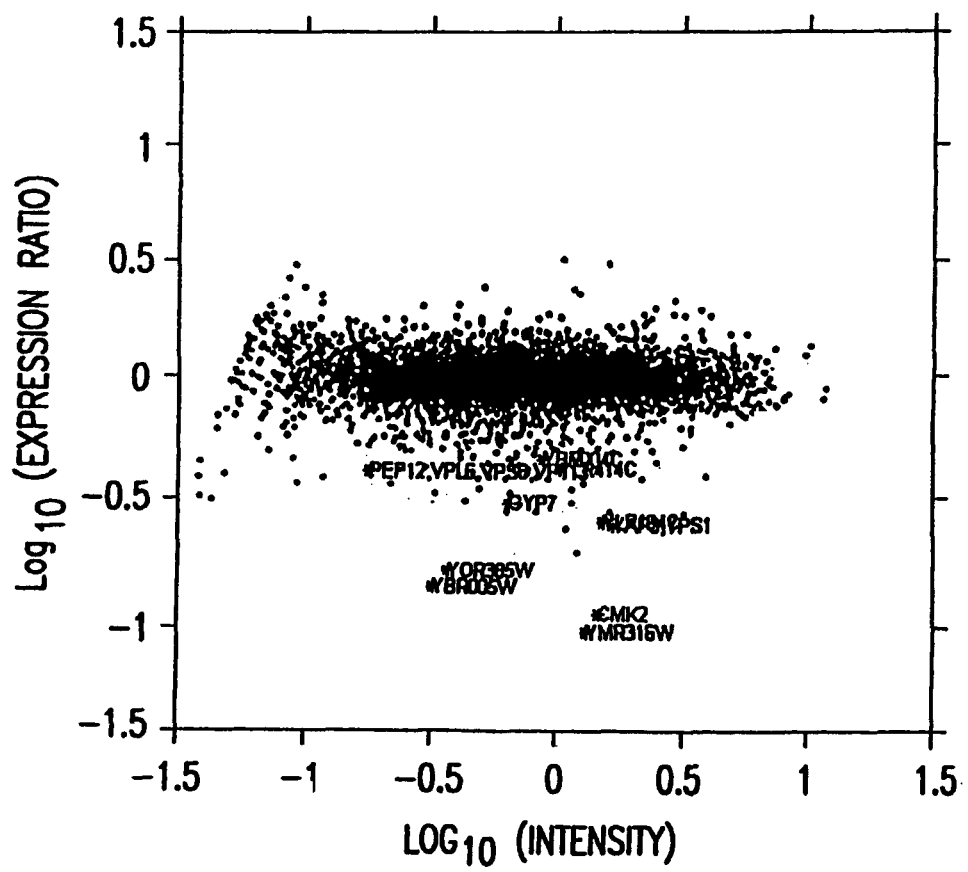
Figure 3:
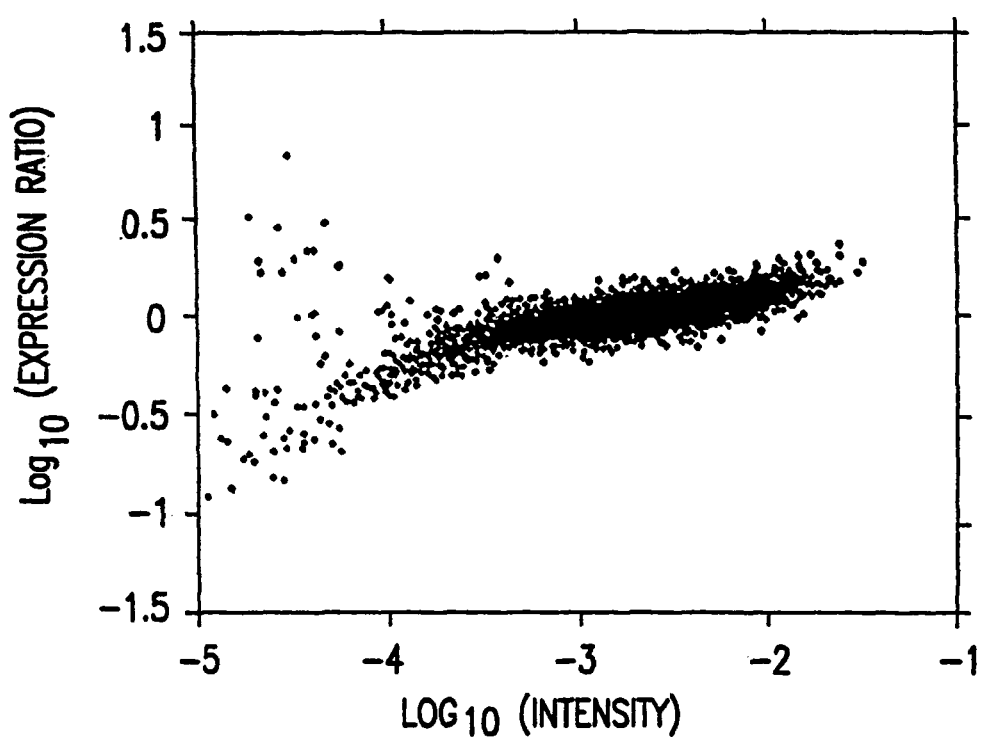

Perturbation: As used herein, a perturbation is the experimental or environmental condition(s) associated with a biological system. Perturbations may be achieved by exposure of a biological system to a drug candidate or pharmacologic agent, the introduction of an exogenous gene into a biological system, the deletion of a gene from the biological system, changes in the culture conditions of the biological system, or any other art recognized method of perturbing a biological system. Further, perturbation of a biological system may be achieved by the onset of disease in the biological system.

Genetic Matter: As used herein, the term "genetic matter" refers to nucleic acids such as messenger RNA ("mRNA"), complementary DNA ("cDNA"), genomic DNA ("gDNA"), DNA, RNA, genes, oligonucleotides, gene fragments, and any combination thereof.

Fluorophore-labeled genetic matter: As used herein, the term "fluorophore-labeled genetic matter" refers to genetic matter that has been labeled with a fluorescently-labeled probe ("fluorophore"). Fluorophores include, but are not limited to, fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992, Nonisotopic DNA Probe Techniques, Academic Press San Diego, Calif.). This DNA may be prepared by reverse transcription of mRNA or by (PCR/IVT) or (IVT) with use of fluorophores as those skilled in the art will appreciate. See e.g. Gelder et al., 1990, "Amplified RNA synthesized from limited quantities of heterogenous cDNA, Proc. Natl. Acad. Sci., USA, 87: 16.63-1667). As used herein, the term PCR refers to the Polymerase Chain Reaction.

Biological System: As used herein, the term "biological system" is broadly defined to include any cell, tissue, organ or multicellular organism. For example, a biological system can be a cell line, a cell culture, a tissue sample obtained from a subject, a *Homo sapien*, a mammal, a yeast substantially isogenic to *Saccharomyces cerevisiae*, or any other art recognized biological system. The state of a biological system can be measured by the content, activities or structures of its cellular constituents. The state of a biological system, as used herein, is determined by the state of a collection of cellular constituents, which are sufficient to characterize the cell or organism for an intended purpose including characterizing the effects of a drug or other perturbation. The term "cellular constituent" encompasses any kind of measurable biological variable. The measurements and/or observations made on the state of these constituents can be of their abundances (i.e., amounts or concentrations in a biological system), their activities, their states of modification (e.g., phosphorylation), or other art recognized measurements relevant to the physiological state of a biological system. In various embodiments, this invention includes making such measurements and/or observations on different collections of cellular constituents. These different collections of cellular constituents are also called aspects of the biological state of a biological system.

One aspect of the biological state of a biological system (e.g., a cell or cell culture) usefully measured in the present invention is its transcriptional state. The transcriptional state of a biological system includes the identities and abundances of the constituent RNA species, especially mRNAs, in the cell under a given set of conditions. Often, a substantial fraction of all constituent RNA species in the biological system are measured, but at least a sufficient fraction is measured to characterize the action of a drug or other perturbation of interest. The transcriptional state of a biological system can be conveniently determined by measuring cDNA abundances by any of several existing gene expression technologies. DNA arrays for measuring mRNA or transcript level of a large number of genes can be employed to ascertain the biological state of a system.

Another aspect of the biological state of a biological system usefully measured is its translational state. The translational state of a biological system includes the identities and abundances of the constituent protein species in the biological system under a given set of conditions. Preferably a substantial fraction of all constituent protein species in the biological system is measured, but at least a sufficient fraction is measured to characterize the action of a drug of interest. The transcriptional state is often representative of the translational state.

Other aspects of the biological state of a biological system are also of use in this invention. For example, the activity state of a biological system includes the activities of the constituent protein species (and also optionally catalytically active nucleic acid species) in the biological system under a given set of conditions. As is known to those of skill in the art, the translational state is often representative of the activity state.

This invention is also adaptable, where relevant, to "mixed" aspects of the biological state of a biological system in which measurements of different aspects of the biological state of a biological system are combined. For example, in one mixed aspect, the abundances of certain RNA species and of certain protein species, are combined with measurements of the activities of certain other protein species. Further, it will be appreciated from the following that this invention is also adaptable to any other aspect of a biological state of a biological system that is measurable.

The biological state of a biological system (e.g., a cell or cell culture) can be represented by a profile of some number of cellular constituents. Such a profile of cellular constituents can be represented by the vector S.

$$S=[S_1, \ldots S_i, \ldots S_k]$$

Where $S_i$ is the level of the i'th cellular constituent, for example, the transcript level of gene i, or alternatively, the abundance or activity level of protein i.

Quantitative Measurement of Cellular Constituents: Microarrays Determining the relative abundance of diverse individual sequences in complex DNA samples is often accomplished using microarrays. See e.g. Shalon et al., 1996, "A Microarray System for Analyzing Complex Samples Using Two-color Fluorescent Probe Hybridization," Genome Research 6:639-645). Frequently, transcript arrays are produced by hybridizing detectably labeled polynucleotides representing the mRNA transcripts present in a cell (e.g., fluorescently labeled cDNA synthesized from total cell mRNA) to a microarray. A microarray is a surface with an ordered array of binding (e.g., hybridization) sites for products of many of the genes in the genome of a cell or organism, preferably most or almost all of the genes. Microarrays are highly reproducible and therefore multiple copies of a given array can be produced and the nominal copies can be compared with each other. Preferably microarrays are small, usually smaller than 5 cm$^2$, and made from materials that are stable under binding (e.g., nucleic acid hybridization) conditions. A given binding site or unique set of binding sites in the microarray will specifically bind the product of a single gene in the cell.

When cDNA complementary to the RNA of a cell is made and hybridized to a microarray under suitable hybridization conditions, the level of hybridization to the site in the array corresponding to any particular gene will reflect the prevalence in the cell of mRNA transcribed from that gene. For example, when detectably labeled (e.g., with a fluorophore) cDNA complementary to the total cellular mRNA is hybridized to a microarray, the site on the array corresponding to a gene (i.e., capable of specifically binding the product of the gene) that is not transcribed in the cell will have little or no signal (e.g., fluorescent signal), and a gene for which the encoded mRNA is prevalent will have a relatively strong signal.

Microarrays are advantageous because nucleic acids representing two different pools of nucleic acid can be hybridized to a microarray and the relative signal from each pool can simultaneously be measured. Each pool of nucleic acids may represent the state of a biological system before and after a perturbation. For example, a first nucleic acid pool may be derived from a mRNA pool from a cell culture before exposing the cell culture to a pharmacological agent and a second cDNA pool may be derived from a mRNA pool derived from the same culture after exposing the culture to a pharmacological agent. Alternatively, the two pools of cDNA could represent pathway responses. Thus, a first cDNA library could be derived from the mRNA of a first aliquot ("pool") of a cell culture that has been exposed to a pathway perturbation and a second cDNA library can be derived from the mRNA of a second aliquot ("pool") of the same cell culture wherein the second aliquot was not exposed to the pathway perturbation. As used herein, microarray experiments, including those described in this section, are referred to as ("differential microarray experiments"). One skilled in the art will appreciate that many forms of differential microarray experiments other than the ones outlined in this disclosure are within the scope of the definition of "differential microarray experiments". Further, as used herein, the term "differential intensity measurement" refers to measurements made in differential microarray experiments. For example, a differential intensity measurement could be the difference between the brightness of a position on a microarray, which corresponds to a cellular constituent of interest, after (i) the microarray has been contacted with DNA derived from a biological system that represents a baseline state and (ii) the microarray has been contacted with DNA derived from a biological system that represents a perturbed state. Further, one skilled in the art will appreciate that the baseline state of a biological system may represent the wild-type state of the biological system. Alternatively, the baseline state of a biological system could represent a different perturbed state of the biological system. Each microarray experiment in a differential microarray experiment, or repeated differential microarray experiment preferably utilizes the same or similar microarray. Microarrays are considered similar if they are prepared from substantially isogenic biological systems and a majority of the binding spots on each microarray are common. Thus, the microarray used in repeated microarray experiments may be the same identical microarray, wherein the microarray is washed between microarray experiments, or the microarray(s) used in repeated microarray experiments may be exact replicas of each other, or they may be similar to each other.

Regardless of the source of the two cDNA pools in differential microarray experiments, each cDNA pool is distinctively labeled with a different dye if the two-fluorophore microarray format is chosen. One skilled in the art will appreciate that certain aspects of the present invention are not limited to the two-fluorophore format. Typically, each cDNA pool is labeled by deriving fluorescently-labeled cDNA by reverse transcription of polyA$^+$RNA in the presence of Cy3-(green) or Cy5-(red) deoxynucleotide triphosphates (Amersham). When the two cDNAs pools are mixed and hybridized to the microarray, the relative intensity of signal from each cDNA set is determined for each site on the array, and any relative difference in abundance of a particular mRNA detected.

When two different fluorescently labeled probes are used, such as CY3 and CY5, the fluorescence emissions at each site of a microarray can be determined using scanning confocal laser microscopy. In one embodiment, a separate scan, using the appropriate excitation line, is carried out for each of the two fluorophores used. Alternatively, a laser may be used that allows simultaneous specimen illumination at wavelengths specific to the two fluorophores and emissions from the two fluorophores can be analyzed simultaneously (See e.g. Shalon et al., supra). The microarrays may be scanned with a laser fluorescent scanner with a computer controlled X-Y stage and a microscope objective. Sequential excitation of the two fluorophores is achieved with a multi-line, mixed gas laser and the emitted light is split by wavelength and detected with two photomultiplier tubes. Fluorescence laser scanning devices are described in Schena et al., 1996, Genome Res. 6: 639-645 and in references cited herein. Alternatively, the fiber-optic bundle described by Ferguson et al., 1996, Nature Biotech. 14: 1681-1684, may be used to monitor mRNA abundance levels at a large number of sites simultaneously.

Signals may be recorded and analyzed by computer, e.g., using a 12 bit analog to digital board. The scanned image may be despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluorophores may be made.

As used herein, the term "microarray experiments" refers to the general class of experiments that are described in this section. One skilled in the art will appreciate that microarray experiments may include the use of a single fluorophore rather than the two-fluorophore example described infra. Further, microarray experiments may be paired. If paired, the first micro rray experiment in the pair could represent a nominal biological system representing a baseline state. The second microarray experiment in the pair could represent the nominal biological system after it has been subjected to a perturbation. Thus comparison of the paired microarray experiment would reveal changes in the state of the nominal biological system based upon the perturbation. Generally, as discussed, supra, these pairs of microarray experiments are referred to as "differential microarray experiments".

Cell Expression Profiles An advantage of using two different cDNA pools in microarray experiments is that a direct and internally controlled comparison of the mRNA levels corresponding to each arrayed gene in two cell states can be made. This and related techniques for quantitative measurement of cellular constituents is generally referred to as cell constituent profiling. Cell constituent profiling is typically expressed as changes, either in absolute level or the ratio of levels, between two known cell conditions, such as a response to treatment of a baseline state with a pharmacological agent, as described in the previous section.

Using the experimental procedures outlined in the preceding section, a ratio of the emission of the two fluorophores may be calculated for any particular hybridization site on a DNA transcript array. This ratio is independent of the absolute expression level of the cognate gene, but is useful for genes whose expression is significantly modulated by drug administration, gene deletion, or any other perturbation. As illustrated in FIGS. 2-6, two-fluorophore cell expression profiles are typically plotted on an x-y graph. The horizontal axis represents the $\log_{10}$ of the ratio of the mean intensity (which approximately reflects the level of expression of a corresponding mRNA derived from a gene) between the first and second pool of cDNA for each site on the microarray. The vertical axis represents the $\log_{10}$ of the ratio of the intensity measured for one fluorescent label, corresponding to the first pool of cDNA, to that measured for the other fluorescent label, corresponding to the second pool of cDNA, for each hybridization site on the microarray.

5.2 Fluorophore Bias Removal

As detailed in the background section the two-color fluorescent hybridization process put forth by Shalon et al., supra, introduces bias into the profile analysis because each species of mRNA that is labeled with fluorophore has a bias in its measured color ratio due to interaction of the fluorescent labeling molecule (fluorophore) with either the reverse transcription of the mRNA or with the hybridization efficiency or both. This bias can be illustrated using the following equations. If we represent the actual molecular abundance of a particular species of mRNA k, representing cellular constituent or gene k in the biological system of interest, as a(k), the color ratio for probe k, ignoring any source of fluorophore bias may be represented as:

$$r_{X/Y} = a_1(k)/a_2(k) \tag{1}$$

where the subscripts 1 and 2 refer to two independently extracted mRNA cultures in which abundances are being compared;
$a_1(k)$ is the abundance of species k in mRNA culture 1;
$a_2(k)$ is the abundance of species k in mRNA culture 2;
subscripts X and Y represent the two different fluorescent labels used; and
$r_{X/Y}$ is the color ratio that ideally reflects abundance ratio $a_1/a_2$.

Equation (1) ideally represents the measurement plotted on the vertical axis of FIGS. 2 thru 6. However the use of a fluorophore labeled deoxynucleotide triphosphates affects the efficiency by which mRNA is reverse transcribed into cDNA and affects the efficiency to which the fluorophore-labeled cDNA hybridizes to the microarray. The precise amount a specific fluorophore affects the transcription or hybridization efficiency is highly dependent upon the precise molecular structure of the fluorophore used. Thus, a direct comparison of $a_1(k)$ to $a_2(k)$, when $a_1(k)$ and $a_2(k)$ are determined using different fluorophores, does not account for these fluorophore-specific affects on transcription and hybridization efficiency. The efficiency of a scanner at determining the abundances $a_1(k)$ and $a_2(k)$ on a microarray is also fluorophore specific. If we represent the combined efficiencies of particular fluorophore in extraction, labeling, reverse transcription, hybridization, and optical scanning as E, a more realistic representation of the color ratio presented in Equation 1 is:

$$r_{X/Y} = a_1(k)E_X(k)/a_2(k)E_Y(k) \tag{2}$$

where
$r_{X/Y}$ is color ratio;
the subscripts 1 and 2 are as defined for equation 1;
$a_1(k)$ and $a_2(k)$ are as defined for equation 1;
subscripts X and Y are two fluorescent labels;
$E_X(k)$ is the efficiency of fluorescent label X; and
$E_Y(k)$ is the efficiency of fluorescent label Y.

In equation 2, Culture 1 has been analyzed using fluorophore X whereas Culture 2 has been analyzed using fluorophore Y. Now the color ratio r is related to the desired abundance ratio $a_1/a_2$ but includes a factor due to the fluorophore specific efficiency biases. If a second hybridization experiment is performed, wherein Culture 1 is now analyzed with fluorophore Y and Culture 2 is analyzed using fluorophore X, the color ratio in the second hybridization experiment may be represented as:

$$r_{X/Y}^{(rev)} = a_2(k)E_X(k)/a_1(k)E_Y(k) \tag{3}$$

where
$r_{X/Y}^{(rev)}$ is color ratio in the reverse experiment; and
$a_2(k)$, $a_1(k)$, $E_X(k)$, and $E_Y(k)$ are as described for equation (2).

Performing hybridization experiments in pairs, with the label assignment reversed in one member of the pair, allows for creation of a combined average measurement in which the fluorophore specific bias is sharply reduced. For example a pair of two-fluorophore hybridization experiments may be performed. The first two-fluorophore experiment would be performed in accordance with equation (2) and the second two-fluorophore hybridization experiments would be performed according to equation (3). If the log of the ratio of the two experiments is taken, the combined experiment can be expressed as:

$$(1/2)(\log(r_{X/Y}) - \log(r_{X/Y}^{rev})) = \log(a_1(k)/a_2(k)) + \tag{4}$$
$$(\log(E_X(k)/E_Y(k)) - \log(E_X(k)/E_Y(k)) = \log(a_1(k)/a_2(k))$$

which is the desired log abundance ratio. Cancellation of the bias terms $\log(E_X(k)/E_Y(k))$ and $\log(E_X(k)/E_Y(k))$ relies on constancy of the biases between the first and second hybridization experiments in each fluorophore-reversed pair. Equation (4) can be written equivalently using ratios as found in equations (1)-(3) instead of differences of log ratios. However, changes in constituent levels are most appropriately expressed as the logarithm of the ratio of abundance in the pair of conditions forming the differential measurement. This is because fold changes are more meaningful than changes in absolute level, biologically.

Figure 4A:
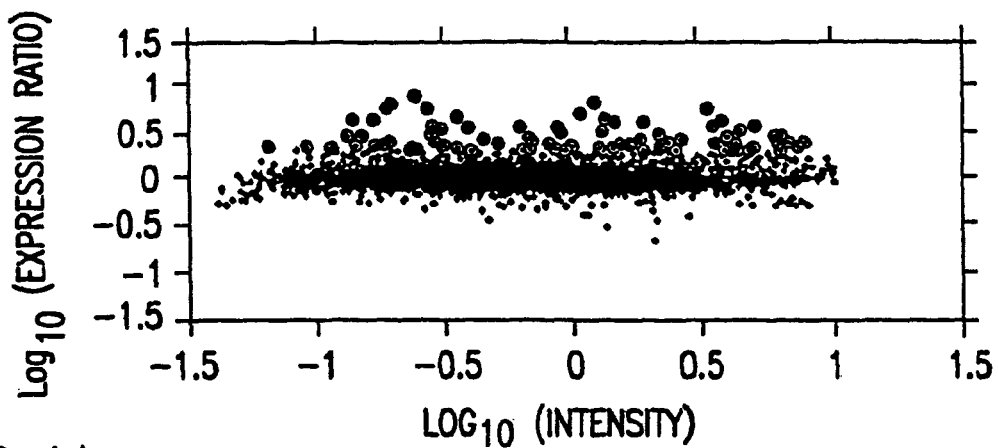
Figure 4B:
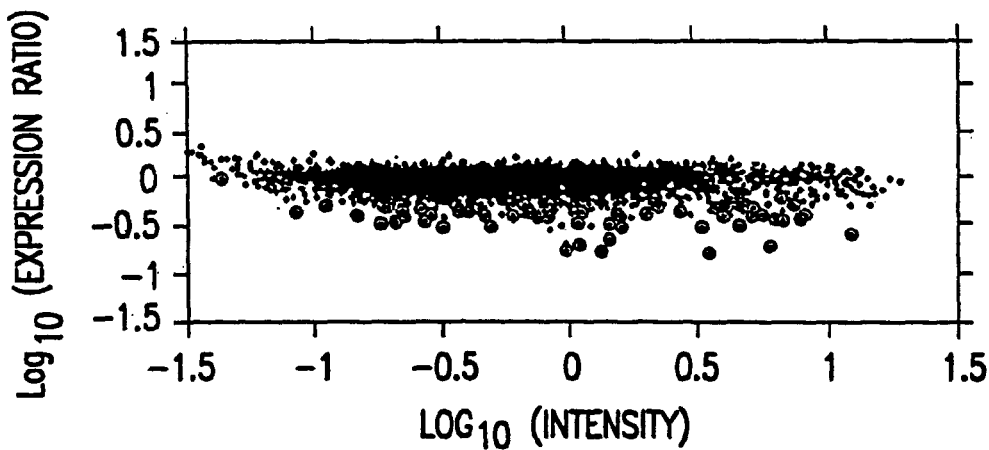
Figure 4C:
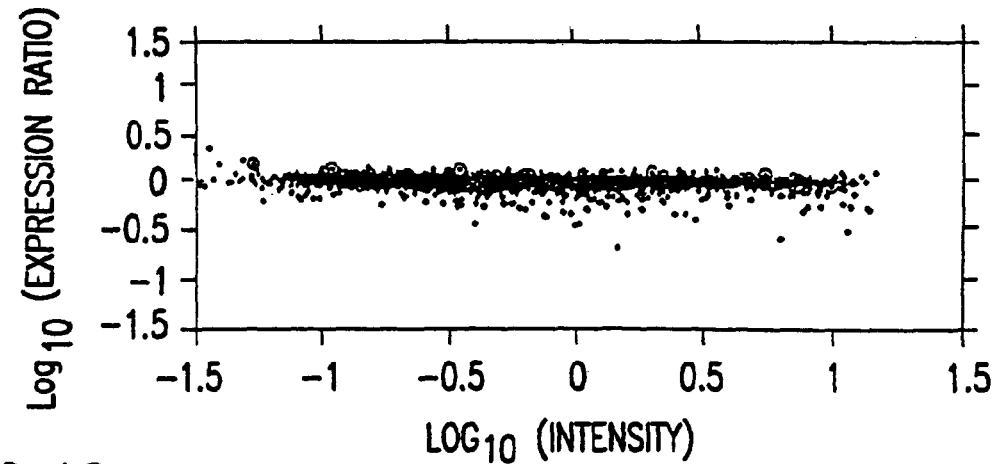

This method of bias removal is particularly useful in two-color hybridization experiments. FIG. 4 illustrates the bias removal method of the present invention. FIG. 4*a* is a color ratio vs. intensity plot for a two-color hybridization experiment in which the two cultures used are nominally the same background strain of the yeast *S. cerevisiae*. Because the two cultures are nominally the same, it is expected that individual spots on the microarray would fluoresce with the same amount of intensity for both of the fluorophores used. Experimental methods are described in the experimental section infra. However, as is readily apparent from FIG. 4*a*, some of the spots on the microarray exhibit fluorophore-specific intensity. For example, spots on the microarray, corresponding to various genes in the yeast *S. cerevisiae*, in which the intensity of the 'red' fluorophore is a factor of two or more greater than the corresponding 'green' intensity are flagged because of their strong fluorophore-specific bias. FIG. 4*b* shows the result of the fluorophore-reversed version of the experiment plotted in FIG. 4*a*. The flagged genes in FIG. 4*b* now have opposite bias. FIG. 4*c* shows the result of combining the data of FIGS. 4*a* and 4*b* according to the methods of the present invention described above. The biases of the flagged genes have been greatly reduced.

The procedure for bias removal as described above may be applied in other contexts. For example, if cultures must be grown at certain positions in an incubator, and harvested in a certain order, the positions and order for two culture types may be reversed in a subsequent experiment and the results combined as described to reduce subtle biases due to temperature or latency differences.

5.3 Combination of Multiple Experiments using Rank-Based Methods

The prior art does not provide a clear method for optimally combining the results of multiple microarray experiments. The results of several experiments could be averaged. However, averaging does not provide information on the statistical significance of any given measurement for each specific gene of interest in the microarray experiments. This section develops a sophisticated method for determining whether the statistical significance of the up- or down-regulation measured for particular genes of interest in multiple microarray experiments. These methods could be applied to nominal repeats of a two-fluorophore DNA micorarray experiment. Alternatively, these methods could be applied to one or more repeats of pairs of experiments, in which the first experiment in the pair represents a baseline state and the second member of the paired repeats represents a biological state after a perturbation has been applied.

If a gene of interest is present in the top 5% of up regulations in a first and second nominal repeat of a microarray experiment, the chance that it appeared that up regulated by chance in both arrays is only 0.05*0.05=0.0025 or 0.25%, assuming systematic biases have been removed. Thus repeating the measurement allows a much higher level of confidence in declaring that the gene of interest is up regulated. In general, if expression ratios in any number of repeated experiments are expressed as percentile rankings, the chance $P(H_0)$ that any (pre-specified) gene of interest is not actually up regulated is $$P(H_0^+) = \prod_i P_i \quad (5)$$

where $P_i$ is the percentile rank in the $i^{th}$ experiment, expressed as a fraction (fifth percentile=0.05). The probability that the gene is not down-regulated is given by $$P(H_0^-) = \prod_i (1 - P_i) \quad (6)$$

These rank-based methods provide a powerful way of reducing false alarms with repeated measurements. For example, setting a threshold at the upper 5% of expression ratios in a hybridization to probes covering the yeast genome, which has approximately 6000 genes, would yield ~6000*0.05=300 false detections in a single experiment, but less than one false detection on average if the same 5% threshold were applied across four experiment repeats $(6000*(0.05)^4)$. This rank combining has the advantage that it does not require any modeling of the detailed error behavior in the underlying hybridization experiments, other than the assumption of no systematic biases. The rank based method is an example of a non-parametric statistical test for the significance of observed up- or down-regulations.

Percentile rankings such as equations (5) and (6) are based upon the assumption that the underlying error behavior is similar for all genes. This is not necessarily the case. For example, in FIG. 5, which plots the expression ratio of two nominative repeats of the same experiment, the weakly expressing genes, as expressed by $\log_{10}$(intensity), have a $\log_{10}$(expression ratio) that deviates from the ideal value of zero. Further, as exhibited by FIG. 5, the weaker expressing a particular gene is, the higher the tendency of the $\log_{10}$(expression ratio) of the gene from two nominal repeats of an experiment to deviate from zero. Thus, the low-abundance (weakly expressing and hence low-intensity hybridization) genes will tend to occupy the tails of the distribution of expression ratios (i.e. deviate from zero in accordance with FIG. 5) more often than the higher-abundance genes.

Figure 5:
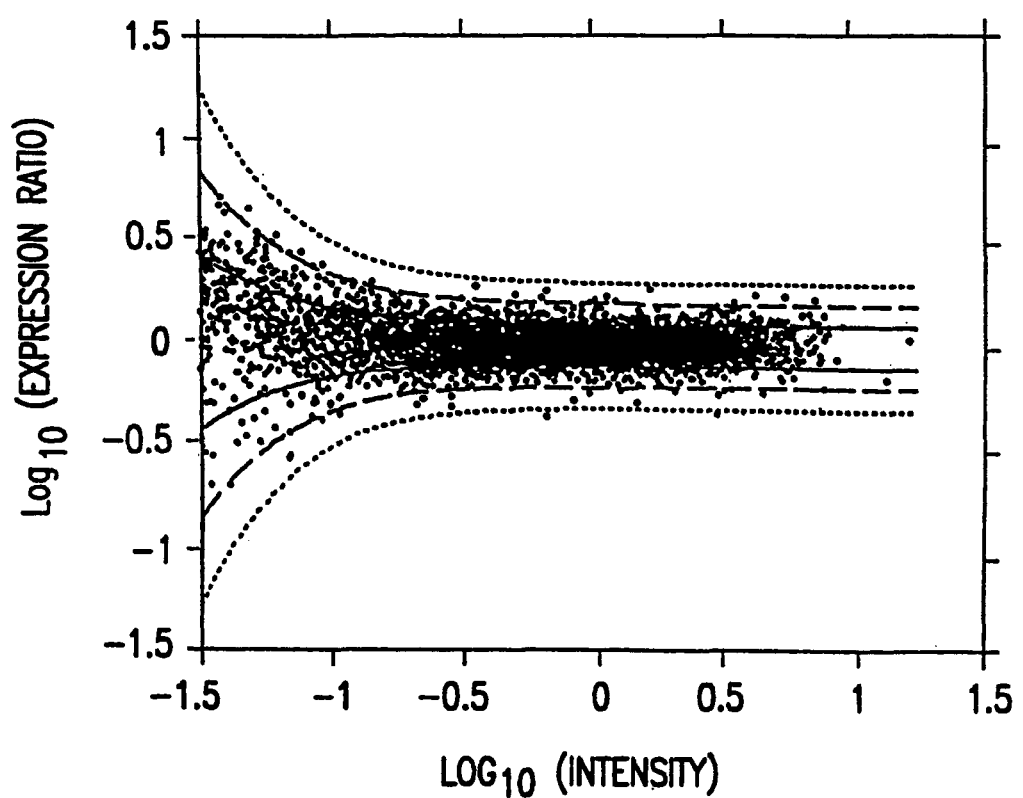

To account for the intensity-dependent error exhibited in hybridization experiments such as the one illustrated by FIG. 5, a measure of up- and down-regulation that makes the error level independent of intensity can be devised. This intensity-independent error level is derived by taking advantage of a statistic that is capable of characterizing the error envelope exhibited in hybridization experiments. This error envelope is illustrated in FIG. 5 by contour lines. The many sources of error that underlie the experiments used to generate plots such as shown in FIG. 5 generally fall into two categories—additive and multiplicative. Therefore the following statistical representation $$d = \frac{(X - Y)}{\sqrt{\sigma_X^2 + \sigma_Y^2 + f^2(X^2 + Y^2)}} \quad (7)$$

where X and Y are the brightness for a probe spot on the microarray with respect to the X and Y fluorophores), $\sigma_X^2$ is a variance term for X and represents the additive error level in the X channel, $\sigma_Y^2$ is a variance term for Y and represents the additive error level in the Y channel, and f is the fractional multiplicative error level, provides a particularly well suited model for fitting the resultant error. Alternatively, X and Y are the brightness of a probe spot corresponding to a cellular constituent of interest derived from a pair of single-fluorophore experiments. In one such embodiment, the first fluorophore (X) may optionally represent a biological system in a base line state whereas the second fluorophore (Y) may represent the biological system in a perturbed state. Regardless of whether a single fluorophore or a dual-fluorophore embodiment is chosen, the fractional multiplicative error, f, is empirically derived by fitting the denominator of equation 7 to the measured data. The denominator of Equation (7) is the expected standard error of the numerator, so d has unit variance. d is therefore an error distribution statistic that is independent of intensity, and therefore applicable to rank methods. Any other definition with the non-parametric properties of equation (7) is also a good variable to use in the rank methods.

According to the methods of the present invention, the denominator of equation (7) is used to generate the intensity independent contour lines shown in FIG. 5. Thus, for example, in FIG. 5, the contour lines gridded at +1 standard deviation have been chosen. Therefore, each contour line above or below zero on the vertical axis (log(Expression Ratio) $\delta$=0) represents an incremental standard deviation of error in accordance with the denominator of equation (7). The choice of using grid lines of ±standard deviation according to the denominator of equation (7) is completely arbitrary. The contour lines could be gridded at any convenient value such as $0.25\sigma$, $0.5\sigma$, $2\sigma$ as long as the contour lines are plotted in accordance with the denominator of equation (7) or a similar nonparamatric representation of error.

From FIG. 5 it is evident that the contour lines follow the error envelope. The value of d is proportional to the number of contours that a particular measurement falls away from log (Expression Ratio)=0. Thus the errors are distributed with respect to the contours similarly at low and at high intensity, and d has the desired property. One advantage of plotting contour lines is that the amount of error associated with each cellular constituent measured on the microarray can be calculated based on information derived from the variance of all the cellular constituents on the microarray across a plurality of measurements. Thus, by using grid lines as plotted in FIG. 5, the significance of any deviation between $X_i$ and $Y_i$, in a two-color fluorescent probe hybridization experiment, where i is a particular cellular constituent, will be placed in the context of the entire error envelope using an equation such as the denominator of equation 7. This provides an intensity independent method for determining the reliability of measurements made of particular cellular constituents in microarray experiments including two-fluorophore or single-fluorophore experiments.

In addition to depending on intensity, error levels also may be gene-specific, again violating the assumption underlying Equations (5) and (6). In this case we may define for any gene, in analogy to Equation (7), $$d = \frac{(X - Y)}{\sigma_{X-Y}} \quad (7.1)$$

where $\sigma_{X-Y}$ is the standard error (rms uncertainty) associated with that gene. This uncertainty may be derived from repeated control experiments where X and Y are derived from the same biological system, in which case $\sigma_{X-Y}$ is the observed standard deviation of X-Y for that gene over the set of experiments. This definition of d then is similarly distributed for all genes, and (5) and (6) may be used with ranking d.

5.4 Combination of Multiple Experiments Using Weighted Average Protocols

Repeated measurements may be combined to yield a quantitative expression level or expression ratio with smaller error bars than individual measurements. Weighting the averaging procedure according to the individual experimental error levels requires knowing or assuming something about the error behavior for each measured quantity. In general, an unbiased weighted mean with minimum variance is achieved by the formula $$x = \frac{\sum (x_i / \sigma_i^2)}{\sum (1 / \sigma_i^2)} \quad (8)$$

where x is the weighted mean of the cellular constituent being measured, $x_i$, and each $\sigma_i^2$ is the variance of an individual $x_i$. See, for example, equation 5-6 in "Data Reduction and Error Analysis for the Physical Sciences", 1969, Bevington, McGraw-Hill, New York, which is incorporated by reference herein in its entirety.

Each $\sigma_i^2$ in equation (8) may be determined in a variety of ways. One approach is to calculate the error envelope for a microarray experiment using two nominal repeats of the two-fluorophore microarray experiment in which the only difference between the two experiments is that the two fluorophores utilized are reversed. See e.g. FIG. 4. Alternatively, only one fluorophore could be utilized. Therefore, there could be no difference at all in the two nominal repeats that are paired in order to determine an error envelope. Such a paired experiment is illustrated in FIG. 5. FIG. 5 also illustrates intensity independent contour lines that are fitted in accordance with the denominator of equation (7). To determine individual $\sigma_i^2$, for each individual measurement i, the intensity ($x_i$) is plotted on the appropriate reference plot, such as FIG. 5. For example, in FIG. 5, the intensity of individual measurements would be plotted along the horizontal axis. Once the horizontal position is determined, $\sigma_i^2$ is calculated based upon the width of the ±1σ intensity independent contour lines at position $x_i$ on the reference plot.

A general formula for the uncertainty of the mean is $$\sigma_x^2 = \frac{1}{\sum \left(\frac{1}{\sigma_i^2}\right)} \quad (9)$$

in accordance with formula 5-10 of "Data Reduction and Error Analysis for the Physical Sciences", supra. Note that when the errors associated with the different nominally repeated measurements are equal, the error in the mean is $N^{-1/2}$ times the individual errors.

In practice the individual errors, $\sigma_i^2$, are themselves uncertain. Inspection of control experiments such as FIG. 5 indicates the rough distribution of errors, but do not indicate whether individual genes at a particular intensity tend to have larger errors due to peculiarities of their RNA extraction or even biological function in the cell. Thus a better estimate of the error in the weighted mean is obtained by adding a component to equation (9) that accounts for scatter in the repeated measurements. If we denote the observed standard deviation for gene j as $s_j$, the error in the mean may be described as:

$$\sigma_x = \frac{1}{N}\left[\left(\sqrt{\frac{1}{\sum_i \frac{1}{\sigma_i^2}}}\right) + (N-1)*s_j\right] \quad (10)$$

where N is the number of repeated measurements. Equation (10) transitions from Equation (9) to the value of the observed scatter, $s_j$, as the number of repeats, N, becomes large. Note that $s_j$ is calculated according to traditional statistical methods, such that $$s_j \cong \frac{1}{N-1}\sum_i (x_i - \bar{x})^2 \quad (11)$$

where N is the number of measurements, $x_i$ are individual measurements of the intensity of gene j in a particular microarray experiment and $\bar{X}$ is the sample mean of the individual measurements. See e.g. equation 2-10 in "Data Reduction and Error Analysis for the Physical Sciences", supra, where $s_j=\sigma^2$. An estimate of the error of the mean, x, as described by equation (10) is necessary because, equations such as (11) require a large number of nominal repeats (N) in order to be a true reflection of error. Estimates of error based on equation (9) do not take into consideration the errors that particular measurement are susceptible to as illustrated in FIG. 1 and as well as gene specific anomalies. One skilled in the art will note that other equations that accomplish the transition from equation (9) to equation (10) are possible.

Figure 6A:
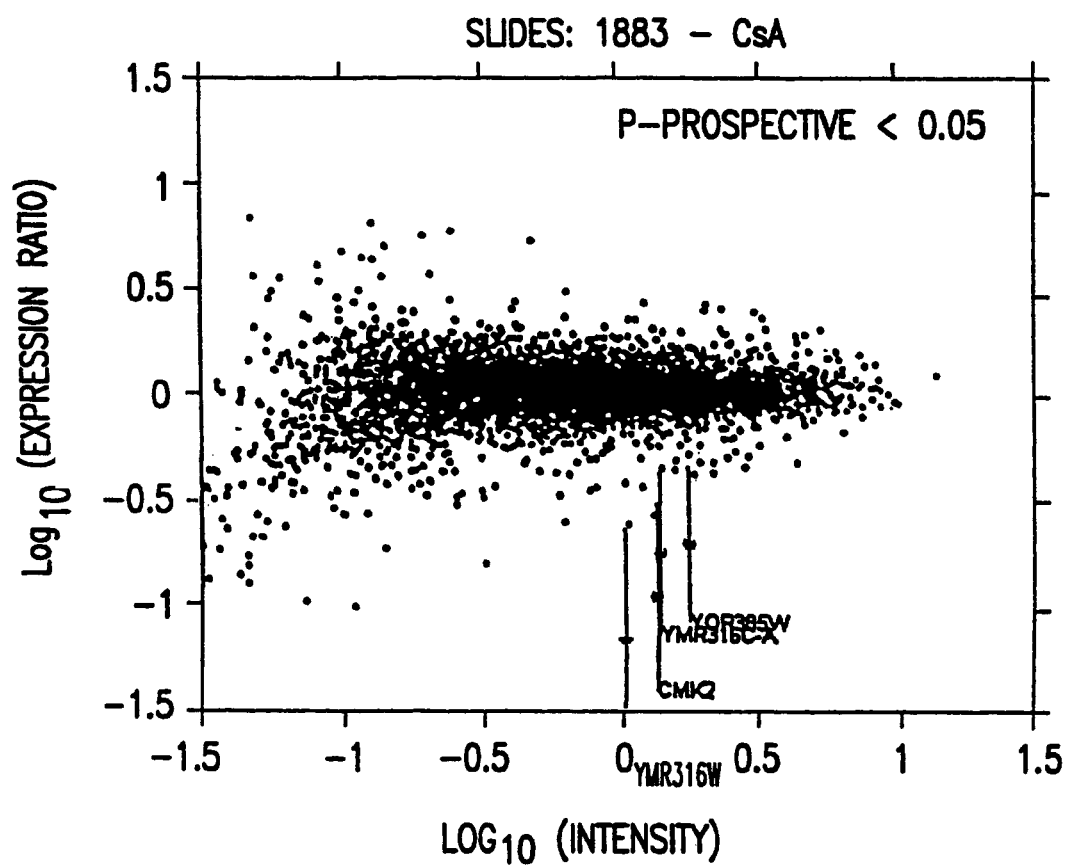
FIG. 6a shows a typical signature plot for a single experiment with the drug Cyclosporin A.
Figure 6B:
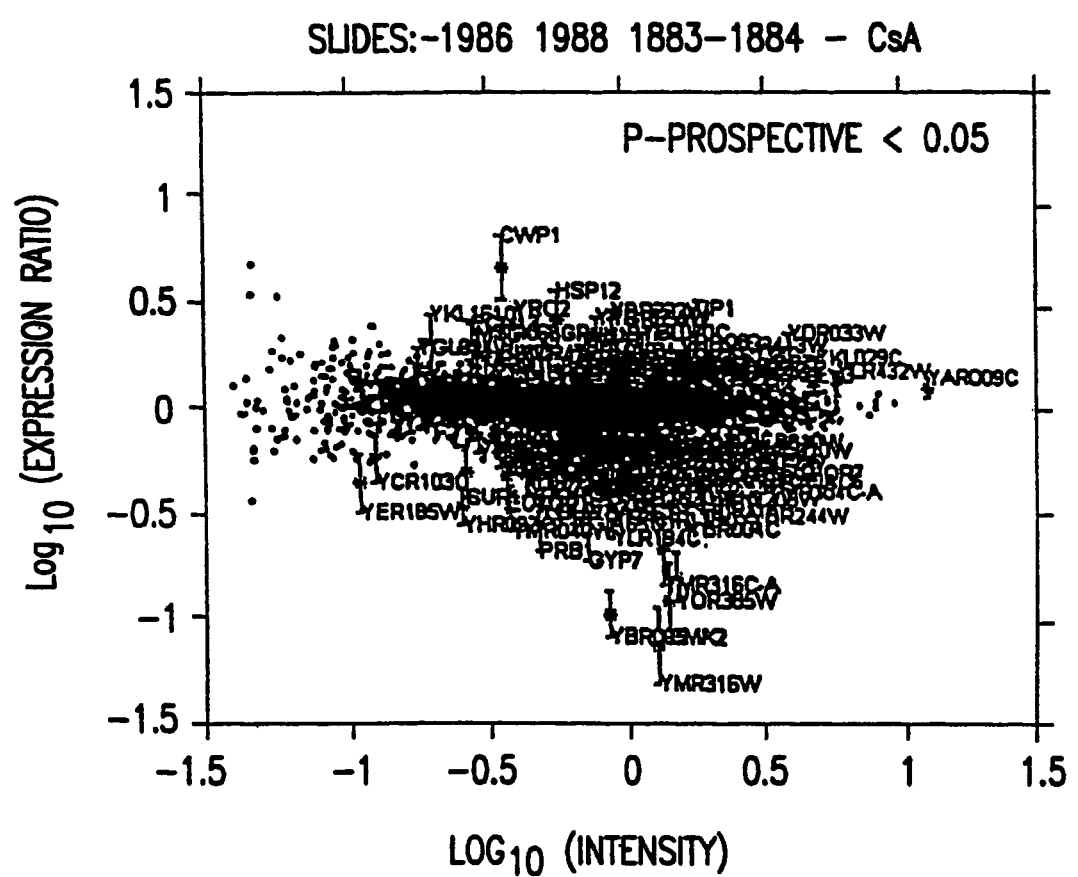

FIG. 6 illustrates the reduction in error obtained with repeated experiments, and the consequent gain in information. FIG. 6a is the signature plot for a single experiment with the drug CsA, obtained as described in the experimental section infra. One sigma error bars have been assigned based on the denominator of equation (7), with values for the additive and multiplicative error levels taken from control experiments. Genes are flagged with their 1-sigma error bars only if they are more than 1.5 sigma from the line log(ratio)=0, i.e. only if they are up- or down-regulated with confidence greater than 95%. FIG. 6b show the results of forming a weighted mean of four repeats (N=4). Here the same criterion of 1.5 sigma has been applied for flagging error bars, but many more genes are flagged. Comparison with FIG. 6a indicates that the number of detections at the 95% confidence has increased from 4 to more than 200 genes. Thus, the example illustrates the additional information about drug response that can be obtained with repeated measurements provided that measurement error is appropriately modeled using equations such as (10).

5.5 Response Profiles

The responses of a biological system to a perturbation, such a pharmacological agent, can be measured by observing the changes in the biological state of the biological system. A response profile is a collection of changes of cellular constituents. The response profile of a biological system (e.g., a cell or cell culture) to the perturbation m may be defined as the vector $v^{(m)}$:

$$v^{(m)} = [v_1^{(m)}, \ldots v_i^{(m)}, \ldots v_k^{(m)}] \quad (12)$$

where $v_i^m$ is the amplitude of response of cellular constituent i under the perturbation m. In some embodiments of response profiles, biological response to the application of a pharmacological agent is measured by the induced change in the transcript level of at least 2 genes, preferably more than 10 genes, more preferably more than 100 genes and most preferably more than 1,000 genes.

In some embodiments, biological response profiles comprise simply the difference between biological variables before and after perturbation. In some preferred embodiments, the biological response is defined as the ratio of cellular constituents before and after a perturbation is applied.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is suitable when most of the smaller responses are expected to be greatly dominated by measurement error. After the truncation, the response vector $v^{(m)}$ also approximates a 'matched detector' (see, e.g., Van Trees, 1968, *Detection, Estimation, and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments of response profiles, perturbations are applied at several levels of strength. For example, different amounts of a drug may be applied to a biological system to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1 + (u/u_0)^n} \quad (13)$$

The adjustable parameters are selected independently for each cellular constituent of the perturbation response. Preferably, the adjustable parameters are selected for each cellular constituent so that the sum of the squares of the differences between the model function (e.g., the Hill function, Equation 13) and the corresponding experimental data at each perturbation strength is minimized. This preferable parameter adjustment method is known in the art as a least squares fit. Other possible model functions are based on polynomial fitting. More detailed description of model fitting and biological response has been disclosed in Friend and Stoughton, Methods of Determining Protein Activity Levels Using Gene Expression Profiles, U.S. Provisional Application Ser. No. 60/084,742, filed on May 8, 1998, which is incorporated herein by reference in it's entirety for all purposes.

5.6 Projected Profiles

The methods of the invention are useful for comparing augmented profiles that contain any number of response profile and/or projected profiles. Projected profiles are best understood after a discussion of genesets, which are co-regulated genes. Projected profiles are useful for analyzing many types of cellular constituents including genesets.

5.6.1 Co-Regulated Genes and Genesets

The use of genesets for representing projected profiles is described in this and the following subsections and is also detailed in U.S. patent application Ser. No. 09/179,569 filed Oct. 27, 1998, now U.S. Pat. No. 6,203,987 dated Mar. 20, 2001, entitled "Methods for using co-regulated genesets to enhance determination and classification of gene expression" by Friend et al., and U.S. patent application Ser. No. 09/220, 275 to filed Dec. 23, 1998 by Friend et al., entitled "Methods for using co-regulated genesets to enhance determination and classification of gene expression" which are both incorporated herein by reference in their entireties. Certain genes tend to increase or decrease their expression in groups. Genes tend to increase or decrease their rates of transcription together when they possess similar regulatory sequence patterns, i.e., transcription factor binding sites. This is the mechanism for coordinated response to particular signaling inputs (see, e.g., Madhani and Fink, 1998, The riddle of MAP kinase signaling specificity, *Transactions in Genetics* 14:151-155; Arnone and Davidson, 1997, The hardwiring of development: organization and function of genomic regulatory systems, *Development* 124:1851-1864). Separate genes which make different components of a necessary protein or cellular structure will tend to co-vary. Duplicated genes (see, e.g., Wagner, 1996, Genetic redundancy caused by gene duplications and its evolution in networks of transcriptional regulators, *Biol. Cybern.* 74:557-567) will also tend to co-vary to the extent mutations have not led to functional divergence in the regulatory regions. Further, because regulatory sequences are modular (see, e.g., Yuh et al., 1998, Genomic cis-regulatory logic: experimental and computational analysis of a sea urchin gene, *Science* 279:1896-1902), the more modules two genes have in common, the greater the variety of conditions under which they are expected to co-vary their transcriptional rates. Separation between modules also is an important determinant since co-activators also are involved.

In summary therefore, for any finite set of conditions, it is expected that genes will not all vary independently, and that there are simplifying subsets of genes and proteins that will co-vary. These co-varying sets of genes form a complete basis in the mathematical sense with which to describe all the profile changes within that finite set of conditions.

5.6.2 Geneset Classification by Cluster Analysis

For many applications, it is desirable to find basis genesets that are co-regulated over a wide variety of conditions. A preferred embodiment for identifying such basis genesets involves clustering algorithms (for reviews of clustering algorithms, see, e.g., Fukunaga, 1990, *Statistical Pattern Recognition*, 2nd Ed., Academic Press, San Diego; Everitt, 1974, *Cluster Analysis*, London: Heinemann Educ. Books; Hartigan, 1975, *Clustering Algorithms*, New York: Wiley; Sneath and Sokal, 1973, *Numerical Taxonomy*, Freeman; Anderberg, 1973, *Cluster Analysis for Applications*, Academic Press: New York).

In some embodiments employing cluster analysis, the expression of a large number of genes is monitored as biological systems are subjected to a wide variety of perturbations. A table of data containing the gene expression measurements is used for cluster analysis. In order to obtain basis genesets that contain genes which co-vary over a wide variety of conditions multiple perturbations or conditions are employed. Cluster analysis operates on a table of data which has the dimension m×k wherein m is the total number of conditions or perturbations and k is the number of genes measured.

A number of clustering algorithms are useful for clustering analysis. Clustering algorithms use dissimilarities or distances between objects when forming clusters. In some embodiments, the distance used is Euclidean distance in multidimensional space:

$$I(x, y) = \left\{ \sum_i (X_i - Y_i)^2 \right\}^{1/2} \quad (14)$$

where I(x,y) is the distance between gene X and gene Y; $X_i$ and $Y_i$ are gene expression response under perturbation i. The Euclidean distance may be squared to place progressively greater weight on objects that are further apart. Alternatively, the distance measure may be the Manhattan distance e.g., between gene X and Y, which is provided by:

$$I(x, y) = \sum_i |X_i - Y_i|^2 \quad (15)$$

Again, $X_i$ and $Y_i$ are gene expression responses under perturbation i. Some other definitions of distances are Chebychev distance, power distance, and percent disagreement. Percent disagreement, defined as I(x,y)=(number of $X_i \neq Y_j$)/i, is particularly useful for the method of this invention, if the data for the dimensions are categorical in nature. Another useful distance definition, which is particularly useful in the context of cellular response, is I=1−r, where r is the correlation coefficient between the response vectors X, Y, also called the normalized dot product X*Y/|X||Y|.

Various cluster linkage rules are useful for defining genesets. Single linkage, a nearest neighbor method, determines the distance between the two closest objects. By contrast, complete linkage methods determine distance by the greatest distance between any two objects in the different clusters. This method is particularly useful in cases when genes or other cellular constituents form naturally distinct "clumps." Alternatively, the unweighted pair-group average defines distance as the average distance between all pairs of objects in two different clusters. This method is also very useful for clustering genes or other cellular constituents to form naturally distinct "clumps." Finally, the weighted pair-group average method may also be used. This method is the same as the unweighted pair-group average method except that the size of the respective clusters is used as a weight. This method is particularly useful for embodiments where the cluster size is suspected to be greatly varied (Sneath and Sokal, 1973, *Numerical taxonomy*, San Francisco: W. H. Freeman & Co.). Other cluster linkage rules, such as the unweighted and weighted pair-group centroid and Ward's method are also useful for some embodiments of the invention. See., e.g., Ward, 1963, *J. Am. Stat Assn.* 58: 236; Hartigan, 1975, *Clustering algorithms*, New York: Wiley.

As the diversity of perturbations in the clustering set becomes very large, the genesets which are clearly distinguishable get smaller and more numerous. However, even ver very large experiment sets, there are small genesets that retain their coherence. These genesets are termed irreducible genesets. Typically, a large number of diverse perturbations are applied to obtain such irreducible genesets.

Often, the clustering of genesets is represented graphically and is termed a 'tree'. Genesets may be defined based on the many smaller branches of a tree, or a small number of larger branches by cutting across the tree at different levels. The choice of cut level may be made to match the number of distinct response pathways expected. If little or no prior information is available about the number of pathways, then the tree should be divided into as many branches as are truly distinct. 'Truly distinct' may be defined by a minimum distance value between the individual branches. Typical values are in the range 0.2 to 0.4 where 0 is perfect correlation and I is zero correlation, but may be larger for poorer quality data or fewer experiments in the training set, or smaller in the case of better data and more experiments in the training set.

Preferably, 'truly distinct' may be defined with an objective test of statistical significance for each bifurcation in the tree. In one aspect of the invention, the Monte Carlo randomization of the experiment index for each cellular constituent's responses across the set of experiments is used to define an objective test.

In some embodiments, the objective test is defined in the following manner:

Let $p_{ki}$ be the response of constituent k in experiment i. Let Π(i) be a random permutation of the experiment index. Then for each of a large (about 100 to 1000) number of different random permutations, construct $p_{k\Pi(i)}$. For each branching in the original tree, for each permutation:

(1) perform hierarchical clustering with the same algorithm ('hclust' in this case) used on the original unpermuted data;

(2) compute fractional improvement f in the total scatter with respect to cluster centers in going from one cluster to two clusters $$f = 1 - \Sigma D_k^{(1)} / \Sigma D_k^{(2)} \quad (16)$$

where $D_k$ is the square of the distance measure for constituent k with respect to the center (mean) of its assigned cluster. Superscript 1 or 2 indicates whether it is with respect to the center of the entire branch or with respect to the center of the appropriate cluster out of the two subclusters. There is considerable freedom in the definition of the distance function D used in the clustering procedure. In these examples, D=1−r, where r is the correlation coefficient between the responses of one constituent across the experiment set vs. the responses of the other (or vs. the mean cluster response).

The distribution of fractional improvements obtained from the Monte Carlo procedure is an estimate of the distribution under the null hypothesis that a given branching was not significant. The actual fractional improvement for that branching with the unpermuted data is then compared to the cumulative probability distribution from the null hypothesis to assign significance. Standard deviations are derived by fitting a log normal model for the null hypothesis distribution. Using this procedure, a standard deviation greater than about 2, for example, indicates that the branching is significant at the 95% confidence level. Genesets defined by cluster analysis typically have underlying biological significance.

Another aspect of the cluster analysis method provides the definition of basis vectors for use in profile projection described in the following sections.

A set of basis vectors V has k×n dimensions, where k is the number of genes and n is the number of genesets.

$$V = \begin{bmatrix} V_1^{(1)} & \cdot & V_1^{(n)} \\ \cdot & \cdot & \cdot \\ V_k^{(1)} & \cdot & V_k^{(n)} \end{bmatrix} \qquad (17)$$

$V^{(n)}_k$ is the amplitude contribution of gene index k in basis vector n. In some embodiments, $V^{(n)}_k=1$, if gene k is a member of geneset n, and $V^{(n)}_k=0$ if gene k is not a member of geneset n. In some embodiments, $V^{(n)}_k$ is proportional to the response of gene k in geneset n over the training data set used to define the genesets.

In some preferred embodiments, the elements $V^{(n)}_k$ are normalized so that each $V^{(n)}_k$ has unit length by dividing by the square root of the number of genes in geneset n. This produces basis vectors which are not only orthogonal (the genesets derived from cutting the clustering tree are disjoint), but also orthonormal (unit length). With this choice of normalization, random measurement errors in profiles project onto the $V^{(n)}_k$ in such a way that the amplitudes tend to be comparable for each n. Normalization prevents large genesets from dominating the results of similarity calculations.

5.6.3 Geneset Classification Based upon Mechanisms of Regulation

Genesets can also be defined based upon the mechanism of the regulation of genes. Genes whose regulatory regions have the same transcription factor binding sites are more likely to be co-regulated. In some preferred embodiments, the regulatory regions of the genes of interest are compared using multiple alignment analysis to decipher possible shared transcription factor binding sites (Stormo and Hartzell, 1989, Identifying protein binding sites from unaligned DNA fragments, *Proc Natl Acad Sci* 86: 1183-1187; Hertz and Stormo, 1995, Identification of consensus patterns in unaligned DNA and protein sequences: a large-deviation statistical basis for penalizing gaps, *Proc of 3rd Intl Conf on Bioinformatics and Genome Research*, Lim and Cantor, eds., World Scientific Publishing Co., Ltd. Singapore, pp. 201-216). For example, as Example 3, infra, shows, common promoter sequence responsive to Gcn4 in 20 genes may be responsible for those 20 genes being co-regulated over a wide variety of perturbations.

The co-regulation of genes is not limited to those with binding sites for the same transcriptional factor. Co-regulated (co-varying) genes may be in the up-stream/down-stream relationship where the products of up-stream genes regulate the activity of down-stream genes. It is well known to those of skill in the art that there are numerous varieties of gene regulation networks. One of skill in the art also understands that the methods of this invention are not limited to any particular kind of gene regulation mechanism. If it can be derived from the mechanism of regulation that two genes are co-regulated in terms of their activity change in response to perturbation, the two genes may be clustered into a geneset.

Because of lack of complete understanding of the regulation of genes of interest, it is often preferred to combine cluster analysis with regulatory mechanism knowledge to derive better defined genesets. In some embodiments, K-means clustering may be used to cluster genesets when the regulation of genes of interest is partially known. K-means clustering is particularly useful in cases where the number of genesets is predetermined by the understanding of the regulatory mechanism. In general, K-mean clustering is constrained to produce exactly the number of clusters desired. Therefore, if promoter sequence comparison indicates the measured genes should fall into three genesets, K-means clustering may be used to generate exactly three genesets with greatest possible distinction between clusters.

5.6.4 Representing Projected Profiles

The expression value of genes can be converted into the expression value for genesets. This process is referred to as projection. In some embodiments, the projection is as follows:

$$P=[P_1, \ldots P_i, \ldots P_n]=p*V \qquad (18)$$

wherein, p is the expression profile, P is the projected profile, $P_i$ is expression value for geneset i and V is a predefined set of basis vectors. The basis vectors have been previously defined in Equation 17 as:

$$V = \begin{bmatrix} V_1^{(1)} & \cdot & V_1^{(n)} \\ \cdot & \cdot & \cdot \\ V_k^{(1)} & \cdot & V_k^{(n)} \end{bmatrix} \qquad (19)$$

wherein $v^{(n)}_k$ is the amplitude of cellular constituent index k of basis vector n.

In one preferred embodiment, the value of geneset expression is simply the average of the expression value of the genes within the geneset. In some other embodiments, the average is weighted so that highly expressed genes do not dominate the geneset value. The collection of the expression values of the genesets is the projected profile.

5.6.5 Profile Comparison and Classification

Once the basis genesets are chosen, projected profiles $P_i$ may be obtained for any set of profiles indexed by i. Similarities between the $P_i$ may be more clearly seen than between the original profiles $p_i$ for two reasons. First, measurement errors in extraneous genes have been excluded or averaged out. Second, the basis genesets tend to capture the biology of the profiles $p_i$ and so are matched detectors for their individual response components. Classification and clustering of the profiles both are based on an objective similarity metric, call it S, where one useful definition is $$S_{ij}=S(P_i,P_j)=P_i*P_j/(|P_i||P_j|) \qquad (20)$$

This definition is the generalized angle cosine between the vectors $P_i$ and $P_j$. It is the projected version of the conventional correlation coefficient between $p_i$ and $p_j$. Profile $p_i$ is deemed most similar to that other profile $p_j$ for which $S_j$ is maximum. New profiles may be classified according to their similarity to profiles of known biological significance, such as the response patterns for known drugs or perturbations in specific biological pathways. Sets of new profiles may be clustered using the distance metric $$D_{ij}=1-S_{ij} \quad (21)$$

where this clustering is analogous to clustering in the original larger space of the entire set of response measurements, but has the advantages just mentioned of reduced measurement error effects and enhanced capture of the relevant biology.

The statistical significance of any observed similarity $S_{ij}$ may be assessed using an empirical probability distribution generated under the null hypothesis of no correlation. This distribution is generated by performing the projection, Equations (19) and (20) for many different random permutations of the constituent index in the original profile p. That is, the ordered set $p_k$ are replaced by $p_{\Pi(k)}$ where $\Pi(k)$ is a permutation, for ~100 to 1000 different random permutations. The probability of the similarity $S_{ij}$ arising by chance is then the fraction of these permutations for which the similarity $S_{ij}$ (permuted) exceeds the similarity observed using the original unpermuted data.

5.7 Methods for Determining Biological Response Profiles

This section provides some exemplary methods for measuring biological responses as well as the procedures necessary to make the reagents used in such methods.

5.7.1 Preparation of Microarrays

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for a product encoded by a gene (e.g., a protein or RNA), and in which binding sites are present for products of most or almost all of the genes in the organism's genome. In a preferred embodiment, the "binding site" (hereinafter, "site") is a nucleic acid or nucleic acid analogue to which a particular cognate cDNA can specifically hybridize. The nucleic acid or analogue of the binding site can be, e.g., a synthetic oligomer, a full-length cDNA, a less-than full length cDNA, or a gene fragment.

Although in a preferred embodiment the microarray contains binding sites for products of all or almost all genes in the target organism's genome, such comprehensiveness is not necessarily required. Usually the microarray will have binding sites corresponding to at least about 50% of the genes in the genome, often at least about 75%, more often at least about 85%, even more often more than about 90%, and most often at least about 99%. Preferably, the microarray has binding sites for genes relevant to the action of a drug of interest or in a biological pathway of interest. A "gene" is an open reading frame (ORF) of preferably at least 50, 75, or 99 amino acids from which a messenger RNA is transcribed in the organism (e.g.; if a single cell) or in some cell in a multicellular organism. The number of genes in a genome can be estimated from the number of mRNAs expressed by the organism, or by extrapolation from a well-characterized portion of the genome. When the genome of the organism of interest has been sequenced, the number of ORFs can be determined and mRNA coding regions identified by analysis of the DNA sequence. For example, the Saccharomyces cerevisiae genome has been completely sequenced and is reported to have approximately 6275 open reading frames (ORFs) longer than 99 amino acids. Analysis of these ORFs indicates that there are 5885 ORFs that are likely to specify protein products (Goffeau et al., 1996, Life with 6000 genes, Science 274: 546-567, which is incorporated by reference in its entirety for all purposes). In contrast, the human genome is estimated to contain approximately $10^5$ genes.

5.7.2 Preparing Nucleic Acids for Microarrays

As noted above, the "binding site" to which a particular cognate cDNA specifically hybridizes is usually a nucleic acid or nucleic acid analogue attached at that binding site. In one embodiment, the binding sites of the microarray are DNA polynucleotides corresponding to at least a portion of each gene in an organism's genome. These DNAs can be obtained by, e.g., polymerase chain reaction (PCR) amplification of gene segments from genomic DNA, cDNA (eg., by RT-PCR), or cloned sequences. PCR primers are chosen, based on the known sequence of the genes or cDNA, that result in amplification of unique fragments (i.e., fragments that do not share more than 10 bases of contiguous identical sequence with any other fragment on the microarray). Computer programs are useful in the design of primers with the required specificity and optimal amplification properties. In the case of binding sites corresponding to very long genes, it will sometimes be desirable to amplify segments near the 3'end of the gene so that when oligo-dT primed cDNA probes are hybridized to the microarray, less-than-full length probes will bind efficiently. Typically each gene fragment on the microarray will be between about 50 bp and about 2000 bp, more typically between about 100 bp and about 1000 bp, and usually between about 300 bp and about 800 bp in length. PCR methods are well known and are described, for example, in Innis et al. eds., 1990, PCR Protocols: A Guide to Methods and Applications, Academic Press Inc., San Diego, Calif., which is incorporated by reference in its entirety for all purposes. An alternative means for generating the nucleic acid for the microarray is by synthesis of synthetic polynucleotides or oligonucleotides, e.g., using N-phosphonate or phosphoramidite chemistries (Froehler et al., 1986, Nucleic Acid Res 14: 5399-5407; McBride et al., 1983, Tetrahedron Lett. 24: 245-248). Synthetic sequences are between about 15 and about 500 bases in length, more typically between about 20 and about 50 bases. In some embodiments, synthetic nucleic acids include non-natural bases, e.g., inosine. As noted above, nucleic acid analogues may be used as binding sites for hybridization. An example of a suitable nucleic acid analogue is peptide nucleic acid (see, e.g., Egholm et al., 1993, PNA hybridizes to complementary oligonucleotides obeying the Watson-Crick hydrogen-bonding rules, Nature 365: 566-568; see also U.S. Pat. No. 5,539,083).

In an alternative embodiment, the binding (hybridization) sites are made from plasmid or phage clones of genes, cDNAs (e.g., expressed sequence tags), or inserts therefrom (Nguyen et al., 1995, Differential gene expression in the murine thymus assayed by quantitative hybridization of arrayed cDNA clones, Genomics 29: 207-209). In yet another embodiment, the polynucleotide of the binding sites is RNA.

5.7.3 Attaching Nucleic Acids to the Solid Surface

The nucleic acid or analogue are attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995, Quantitative monitoring of gene expression patterns with a complementary microarray, Science 270: 467-470. This method is especially useful for preparing microarrays of cDNA. See also DeRisi et al., 1996, Use of a cMicroarray to analyze gene expression patterns in human cancer, Nature Genetics 14: 457-460; Shalon et al., 1996, A microarray system for analyzing complex DNA samples using two-color fluorescent probe hybridization, Genome Res. 6: 639-645; and Schena et al., 1995, Parallel human genome analysis; microarray-based expression of 1000 genes, Proc. Natl. Acad. Sci. USA 93: 10539-11286.

A second preferred method for making microarrays is by making high-density oligonucleotide arrays. Techniques are known for producing arrays containing thousands of oligonucleotides complementary to defined sequences, at defined locations on a surface using photolithographic techniques for synthesis in situ (see, Fodor et al., 1991, Light-directed spatially addressable parallel chemical synthesis, Science 251: 767-773; Pease et al., 1994, Light-directed oligonucleotide arrays for rapid DNA sequence analysis, Proc. Natl. Acad. Sci. USA 91: 5022-5026; Lockhart et al., 1996, Expression monitoring by hybridization to high-density oligonucleotide arrays, Nature Biotech 14: 1675; U.S. Pat. Nos. 5,578,832; 5,556,752; and 5,510,270, each of which is incorporated by reference in its entirety for all purposes) or other methods for rapid synthesis and deposition of defined oligonucleotides (Blanchard et al., 1996, High-Density Oligonucleotide arrays, Biosensors & Bioelectronics 11: 687-90). When these methods are used, oligonucleotides (e.g., 20-mers) of known sequence are synthesized directly on a surface such as a derivatized glass slide. Usually, the array produced contains multiple probes against each target transcript. Oligonucleotide probes can be chosen to detect alternatively spliced mRNAs or to serve as various type of control.

Another preferred method of making microarrays is by use of an inkjet printing process to synthesize oligonucleotides directly on a solid phase, as described, e.g., in co-pending U.S. patent application Ser. No. 09/008,120 filed on Jan. 16, 1998, by Blanchard entitled "Chemical Synthesis Using Solvent Microdroplets", which is incorporated by reference herein in its entirety.

Other methods for making microarrays, e.g., by masking (Maskos and Southern, 1992, Nuc. Acids Res. 20: 1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, as will be recognized by those of skill in the art, very small arrays will be preferred because hybridization volumes will be smaller.

5.7.4 Generating Labeled Probes

Methods for preparing total and poly(A)+ RNA are well known and are described generally in Sambrook et al., supra. In one embodiment, RNA is extracted from cells of the various types of interest in this invention using guanidinium thiocyanate lysis followed by CsCl centrifugation (Chirgwin et al., 1979, Biochemistry 18: 5294-5299). Poly(A)+ RNA is selected by selection with oligo-dT cellulose (see Sambrook et al., supra). Cells of interest include wild-type cells, drug-exposed wild-type cells, modified cells, and drug-exposed modified cells.

Labeled cDNA is prepared from mRNA by oligo dT-primed or random-primed reverse transcription, both of which are well known in the art (see, e.g., Klug and Berger, 1987, Methods Enzymol. 152: 316-325). Reverse transcription may be carried out in the presence of a DNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, Expression monitoring by hybridization to high-density oligonucleotide arrays, Nature Biotech. 14: 1675, which is incorporated by reference in its entirety for all purposes). In alternative embodiments, the cDNA or RNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent.

When fluorescently-labeled probes are used, many suitable fluorophores are known, including fluorescein, lissamine, phycoerythrin, rhodamine (Perkin Elmer Cetus), Cy2, Cy3, Cy3.5, Cy5, Cy5.5, Cy7, Fluor X (Amersham) and others (see, e.g., Kricka, 1992, Nonisotopic DNA Probe Techniques, Academic Press San Diego, Calif.). It will be appreciated that pairs of fluorophores are chosen that have distinct emission spectra so that they can be easily distinguished.

In another embodiment, a label other than a fluorescent tabel is used. For example, a radioactive label, or a pair of radioactive labels with distinct emission spectra, can be used (see Zhao et al., 1995, High density cDNA filter analysis: a novel approach for large-scale, quantitative analysis of gene expression, Gene 156: 207; Pietu et al., 1996, Novel gene transcripts preferentially expressed in human muscles revealed by quantitative hybridization of a high density cDNA array, Genome Res. 6: 492). However, because of scattering of radioactive particles, and the consequent requirement for widely spaced binding sites, use of radioisotopes is a less-preferred embodiment.

In one embodiment, labeled cDNA is synthesized by incubating a mixture containing 0.5 mM dGTP, DATP and dCTP plus 0.1 mM dTTP plus fluorescent deoxyribonucleotides (e.g., 0.1 mM Rhodamine 110 UTP (Perken Elmer Cetus) or 0.1 mM Cy3 dUTP (Amersham)) with reverse transcriptase (e.g., SuperScript™II, LTI Inc.) at 42° C. for 60 minutes.

5.7.5 Hybridization to Microarrays

Nucleic acid hybridization and wash conditions are optimally chosen so that the probe "specifically binds" or "specifically hybridizes" to a specific array site, i.e., the probe hybridizes, duplexes or binds to a sequence array site with a complementary nucleic acid sequence but does not hybridize to a site with a non-complementary nucleic acid sequence. One polynucleotide sequence is considered complementary to another when, if the shorter of the polynucleotides is less than or equal to 25 bases, there are no mismatches using standard base-pairing rules or, if the shorter of the potynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., supra).

Optimal hybridization conditions will depend on the length (e.g., oligomer versus polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., 1987, Current Protocols in Molecular Biology, Greene Publishing and Wiley-Interscience, New York. When the microarrays of Schena et al. are used, typical hybridization conditions are hybridization in 5×SSC plus 0.2% SDS at 65° C. for 4 hours followed by washes at 25° C. in low stringency wash buffer (1×SSC plus 0.2% SDS) followed by 10 minutes at 25° C. in high stringency wash buffer (0.1×SSC plus 0.2% SDS) (Shena et al., 1996, Proc. Natl. Acad. Sci. USA, 93: 10614). Useful hybridization conditions are also provided in, e.g., Tijessen, 1993, Hybridization With Nucleic Acid Probes, Elsevier Science Publishers B. V. and Kricka, 1992, Nonisotopic DNA Probe Techniques, Academic Press San Diego, Calif.

5.8 Computer Implementations

Figure 7:
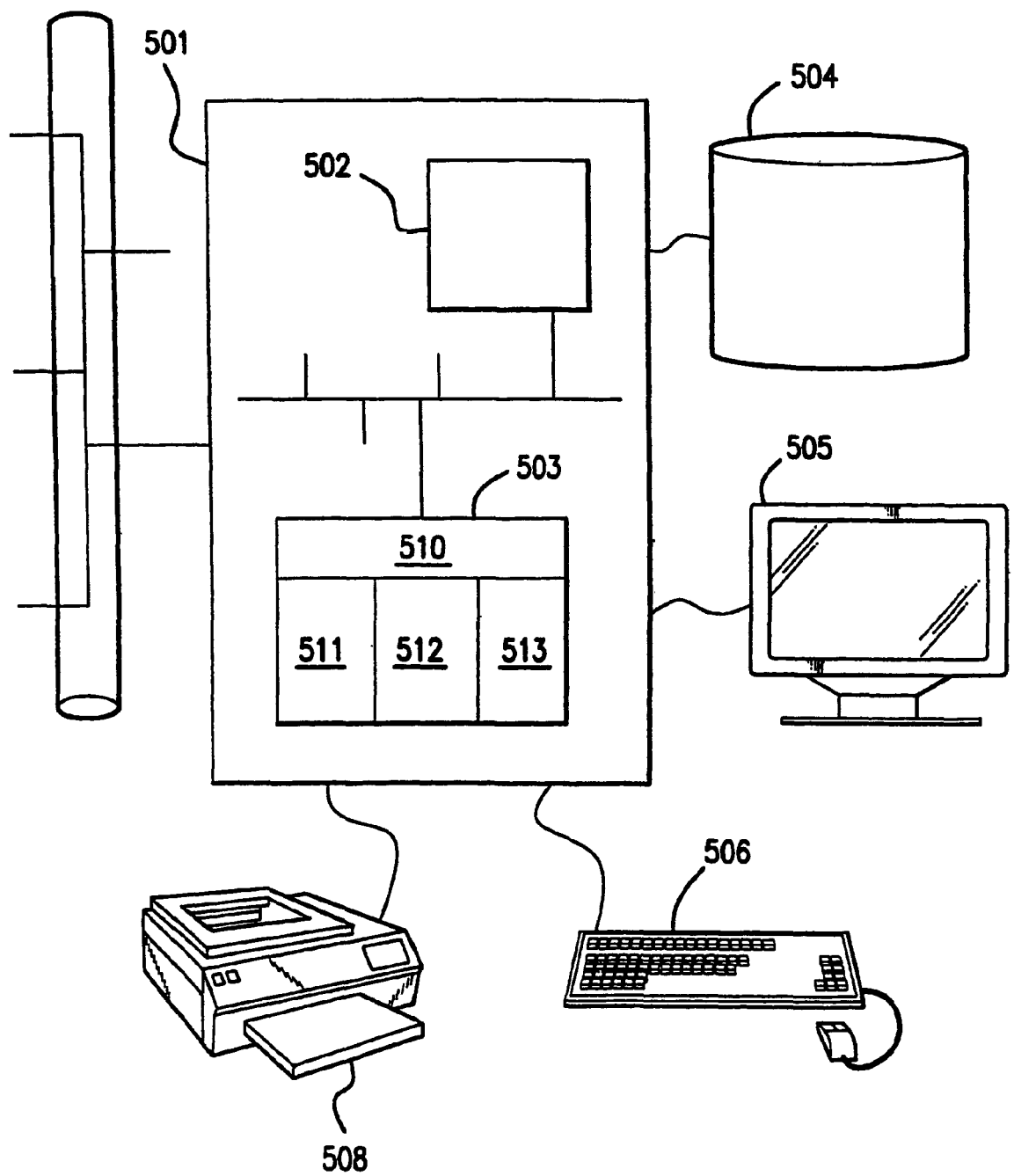
FIG. 7 illustrates a computer system useful for embodiments of the invention.

The analytic methods described in the previous sections can be implemented by use of the following computer systems and according to the following programs and methods. FIG. 7 illustrates an exemplary computer system suitable for implementation of the analytic methods of this invention. Computer system 501 is illustrated as comprising internal components and being linked to external components. The internal components of this computer system include processor element 502 interconnected with main memory 503. For example, computer system 501 can be an Intel 8086-, 80386-, 80486-, Pentium®, or Pentium®-based processor with preferably 32 MB or more of main memory.

The external components include mass storage 504. This mass storage can be one or more hard disks (which are typically packaged together with the processor and memory). Such hard disks are preferably of 1 GB or greater storage capacity. Other external components include user interface device 505, which can be a monitor, together with inputing device 506, which can be a "mouse", or other graphic input devices (not illustrated), and/or a keyboard. A printing device 508 can also be attached to the computer 501.

Typically, computer system 501 is also linked to network link 507, which can be part of ah Ethernet link to other local computer systems, remote computer systems, or wide area communication networks, such as the Internet. This network link allows computer system 501 to share data and processing tasks with other computer systems.

Loaded into memory during operation of this system are several software components, which are both standard in the art and special to the instant invention. These software components collectively cause the computer system to function according to the methods of this invention. These software components are typically stored on mass storage 504. Software component 510 represents the operating system, which is responsible for managing computer system 501 and its network interconnections. This operating system can be, for example, of the Microsoft Windows' family, such as Windows 3.1, Windows 95, Windows 98, or Windows NT. Software component 511 represents common languages and functions conveniently present on this system to assist programs implementing the methods specific to this invention. Many high or low level computer languages can be used to program the analytic methods of this invention. Instructions can be interpreted during run-time or compiled. Preferred languages include C/C++, FORTRAN and JAVA®. Most preferably, the methods of this invention are programmed in mathematical software packages that allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, IL), or S-Plus from Math Soft (Cambridge, Mass.). Accordingly, software component 512 and/or 513 represents the analytic methods of this invention as programmed in a procedural language or symbolic package. In an exemplary implementation, to practice the methods of the present invention, a user first loads differential microarray experiment data into the computer system 501. These data can be directly entered by the user from monitor 505, keyboard 506, or from other computer systems linked by network connection 507, or on removable storage media such as a CD-ROM, floppy disk (not illustrated), tape drive (not illustrated), ZIP® drive (not illustrated) or through the network (507). Next the user causes execution of expression profile analysis software 512 which performs the methods of the present invention.

In another exemplary implementation, a user first loads microarray experiment data into the computer system. This data is loaded into the memory from the storage media (504) or from a remote computer, preferably from a dynamic geneset database system, through the network (507). Next the user causes execution of software that performs the steps of fluorophore bias removal, the rank-based methods of the present invention or the weighted averaging protocols of the present invention.

Alternative computer systems and software for implementing the analytic methods of this invention will be apparent to one of skill in the art and are intended to be comprehended within the accompanying claims. In particular, the accompanying claims are intended to include the alternative program structures for implementing the methods of this invention that will be readily apparent to one of skill in the art.

6 EXPERIMENTAL

The following section details how reagents are prepared for the experiments illustrated in FIGS. 2-6.

Construction, Growth and Drug-Treatment of Yeast Strains

The strains used in this study were constructed by standard techniques. See e.g. Schiestl et al., 1993, Introducing DNA into yeast by transformation, *Methods: A companion to Methods in Enzymology* 5: 79-85. For experiments involving FK506, cells were grown for three generations to a density of $1 \times 10^7$ cells/ml in YAPD medium (YPD plus 0.004% adenine) supplemented with 10 mM calcium chloride as previously described by Garrett-Engele et al., 1995, Calcineurin, the $Ca^{2+}$/calmodulin-dependent protein phosphatase, is essential in yeast mutants with cell integrity defects and in mutants that lack functional vacuolar H(+)-ATPase, *Mol. Cell. Biol.* 15: 4103-4114. Where indicated, FK506 was added to a final concentration of 1 μg/ml 0.5 hr after inoculation of the culture. Cyclosporin A (CsA) was added to a concentration of 30 μg/ml. Cells were broken by standard procedures (See e.g. Ausubel et al., Current Protocols in Molecular Biology, John Wiley & Sons, Inc. (New York), 12.12.1-13.12.5) with the following modifications. Cell pellets were resuspended in breaking buffer (0.2M Tris HCl pH 7.6, 0.5M NaCl, 10 mM EDTA, 1% SDS), vortexed for 2 minutes on a VWR multitube vortexer at setting 8 in the presence of 60% glass beads (425-600 μm mesh; Sigma) and phenol:chloroform (50: 50, v/v). Following separation, the aqueous phase was reextracted and ethanol precipitated. Poly $A^+$ RNA was isolated by two sequential chromatographic purifications over oligo dT cellulose (NEB) using established protocols. See e.g. Ausubel et al., supra).

Preparation and Hybridization of the Labeled Sample

Fluorescently-labeled cDNA Was prepared, purified and hybridized essentially as described by DeRisi et al. DeRisi et al., 1997, Exploring the metabolic and genetic control of gene expression on a genomic scale, *Science* 278: 680-686. Briefly, Cy3- or Cy5-dUTP (Amersham) was incorporated into cDNA during reverse transcription (Superscript II, LTI, Inc.) And purified by concentrating to less than 10 μl using Micron-30 microconcentrators (Amicon). Paired cDNAs were resuspended in 20-26 μl hybridization solution (3×SSC, 0.75 μg/ml poly A DNA, 0.2% SDS) and applied to the microarray under a 22×30 mm coverslip for 6 hr at 63° C., all according to DeRisi et al., (1997), supra.

Fabrication and Scanning of Microarrays

PCR products containing common 5' and 3' sequences (Research Genetics) were used as templates with amino-modified forward primer and unmodified reverse primers to PCR amplify 6065 ORFs from the *S. cerevisiae* genome. First pass success rate was 94%. Amplification reactions that gave products of unexpected sizes were excluded from subsequent analysis. ORFs that could not be amplified from purchased templates were amplified from genomic DNA. DNA samples form 100 µl reactions were isopropanol precipitated, resuspended in water, brought to 3×SSC in a total volume of 15 and transferred to 384-well microtiter plates (Genetix). PCR products were spotted onto 1×3 inch polylysine-treated glass slides by a robot built according to specifications provided in Schena et al., supra; DeRisi et al., 1996, Discovery and analysis of inflammatory disease-related genes using micorarrays, *PNAS USA*, 94:2150-2155; and DeRisi et al., (1997). After printing, slides were processed following published protocols. See DeRisi et al., (1997).

Microarrays were images on a prototype multi-frame CCD camera in development at Applied Precision, Inc. (Seattle, Wash.). Each CCD image frame was approximately 2 mm square. Exposure time of 2 seconds in the Cy5 channel (white light through Chroma 618-648 nm excitation filter, Chroma 657-727 nm emission filter) and 1 second in the Cy3 channel (Chroma 535-560 nm excitation filter, Chroma 570-620 nm emission filter) were done consecutively in each frame before moving to the next, spatially contiguous frame. Color isolation between the Cy3 and Cy5 channels was ~100:1 or better. Frames were knitted together in software to make the complete images. The intensity of spots (~100 µm) was quantified from the 10 µm pixels by frame background subtraction and intensity averaging in each channel. Dynamic range of the resulting spot intensities was typically a ratio of 1000 between the brightest spots and the background-subtracted additive error level. Normalization between the channels was accomplished by normalizing each channel to the mean intensities of all genes. This procedure is nearly equivalent to normalization between channels using the intensity ratio of genomic DNA spots (See DeRisi et al., 1997)[11], but is possibly more robust since it is based on the intensities of several thousand spots distributed over the array.

Determination of Signature Correlation Coefficients and their Confidence Limits

Correlation coefficients between the signature ORFs of various experiments were calculated using $$\rho = \sum_k x_k y_k \bigg/ \left( \sum_k x_k^2 \sum_k y_k^2 \right)^{1/2}$$

where $x_k$ is the $\log_{10}$ of the expression ratio for the k'th gene in the x signature, and $y_k$ is the $\log_{10}$ of the expression ratio for the k'th gene in the y signature. The summation is over those genes that were either up- or down-regulated in either experiment at the 95% confidence level. These genes each had a less than 5% chance of being actually unregulated (having expression ratios departing from unity due to measurement errors alone). This confidence level was assigned based on an error model which assigns a lognormal probability distribution to each gene's expression ratio with characteristic width based on the observed scatter in its repeated measurements (repeated arrays at the same nominal experimental conditions) and on the individual array hybridization quality. This latter dependence was derived from control experiments in which both Cy3 and Cy5 samples were derived from the same RNA sample. For large numbers of repeated measurements the error reduces to the observed scatter. For a single measurement the error is based on the array quality and the spot intensity.

Random measurement errors in the x and y signatures tend to bias the correlation toward zero. In most experiments the great majority of genes is not significantly affected but do exhibit small random measurement errors. Selecting only the 95% confidence genes for the correlation calculation, rather than the entire genome, reduces this bias and makes the actual biological correlations more apparent.

Correlations between a profile and itself are unity by definition. Error limits on the correlation are 95% confidence limits based on the individual measurement error bars, and assuming uncorrelated errors. They do not include the bias mentioned above; thus, a departure of p from unity does not necessarily mean that the underlying biological correlation is imperfect. However, a correlation of 0.7±0.1, for example, is very significantly different from zero. Small (magnitude of $\rho<0.2$) but formally significant correlation in the tables and text probably are due to small systematic biases in the Cy5/Cy3 ratios which violate the assumption of independent measurement errors used to generate the 95% confidence limits. Therefore, these small correlation values should be treated as not significant. A likely source of uncorrected systematic bias is the partially corrected scanner detector nonlinearity that differentially affects the Cy3 and Cy5 detection channels.

The 1 µg/ml FK506 treatment signature was compared to over 40 unrelated deletion mutant or drug signatures. These control profiles had correlation coefficients with the FK506 profile which were distributed around zero (mean p=−0.03) with a standard deviation of 0.16 (data not shown) and none had correlations greater than p=0.38. Similarly, the calcineurin mutant signature correlated well with the CsA-treatment signature ($\rho=0.71\pm0.04$) but not with the signatures from the negative control signatures (mean $\Theta=-0.02$ with a standard deviation of 0.18).

Quality Controls

End-to-end checks on expression ratio measurement accuracy were provided by analyzing the variance in repeated hybridizations using the same mRNA labeled with both Cy3 and Cy5, and also using Cy3 and Cy5 mRNA samples isolated from independent cultures of the same nominal strain and conditions. Biases undetected with this procedure, such as gene-specific biases presumably due to differential incorporation of Cy3- and Cy5-dUTP into cDNA, were minimized by performing hybridizations in fluorophore-reversed pairs, in which the Cy3/Cy5 labeling of the biological conditions was reversed in one experiment with respect to the other. The expression ratio for each gene is then the ratio of ratios between the two experiments in the pair. Other biases are removed by algorithmic numerical detrending. The magnitude of these biases in the absence of detrending and fluorophore reversal is typically on the order of 30% in the ratio, but may be as high as twofold for some ORFs.

Expression ratios are based on mean intensities over each spot. The occasional smaller spots have fewer image pixels in the average. This does not degrade accuracy noticeably until the number of pixels falls below ten, in which case the spot is rejected from the data set. Wander of spot positions with respect to the nominal grid is adaptively tracked in array subregions by the image processing software. Unequal spot wander within a subregion greater than half a spot spacing is problematic for the automated quantitating algorithms; in this case the spot is rejected from analysis based on human inspection of the wander. Any spots partially overlapping are excluded from the data set. Less than 1% of spots typically are rejected for these reasons.

7 REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A computer program product embodied on a computer readable storage medium, the computer readable storage medium encoded with computer-executable instructions which, when executed by a processor, cause the processor to execute a method of reducing fluorophore-specific bias in gene expression data comprising:
   receiving a first plurality, second plurality, third plurality, and fourth plurality of fluorescent emission signals obtained from a two color hybridization microarray experiment comprising steps (1)-(10):
   (1) labeling a first pool of genetic matter, derived from a biological system representing a baseline state, with a first fluorophore to obtain a first pool of fluorophore-labeled genetic matter;
   (2) labeling a second pool of genetic matter, derived from a biological system representing a perturbed state, with a second fluorophore to obtain a second pool of fluorophore-labeled genetic matter;
   (3) labeling a third pool of genetic matter, derived from said biological system representing said baseline state, with said second fluorophore to obtain a third pool of fluorophore-labeled genetic matter;
   (4) labeling a fourth pool of genetic matter, derived from said biological system representing said perturbed state, with said first fluorophore to obtain a fourth pool of fluorophore-labeled genetic matter;
   (5) contacting said first pool of fluorophore-labeled genetic matter and said second pool of fluorophore-labeled genetic matter with a first microarray under conditions such that hybridization can occur;
   (6) detecting said first plurality of fluorescent emission signals at each of a plurality of discrete loci on the first microarray from said first pool of fluorophore-labeled genetic matter that becomes bound to said first microarray under said conditions;
   (7) detecting said second plurality of fluorescent emission signals at each of said plurality of discrete loci on the first microarray from said second pool of fluorophore-labeled genetic matter that becomes bound to said first microarray under said conditions;
   (8) contacting said third pool of fluorophore-labeled genetic matter and said fourth pool of fluorophore-labeled genetic matter with a second microarray under conditions such that hybridization can occur;
   (9) detecting said third plurality of fluorescent emission signals at each of said plurality of discrete loci on the second microarray from said third pool of fluorophore-labeled genetic matter that becomes bound to said second microarray under said conditions; and
   (10) detecting said fourth plurality of fluorescent emission signals at each of said plurality of discrete loci on the second microarray from said fourth pool of fluorophore-labeled genetic matter that becomes bound to said second microarray under said conditions;
   wherein:
   said first microarray and said second microarray are similar to each other, exact replicas of each other, or are identical; and
   said first fluorophore and said second fluorophore are different;
   wherein the computer readable storage medium comprises computer executable instructions for:
   normalizing a first fluorescent emission signal by a first mean intensity, said first fluorescent emission signal being measured at a first discrete locus of the plurality of discrete loci on the first microarray, said first mean intensity being the mean intensity of the first plurality of fluorescent emission signals measured at each of the plurality of discrete loci on the first microarray, thereby calculating a first normalized fluorescent emission signal;
   normalizing a second fluorescent emission signal by a second mean intensity, said second fluorescent emission signal being measured at said first discrete locus, said second mean intensity being the mean intensity of the second plurality of fluorescent emission signals measured at each of the plurality of discrete loci on the first microarray, thereby calculating a second normalized fluorescent emission signal;
   determining a first color ratio between said first normalized fluorescent emission signal and said second normalized fluorescent emission signal;
   normalizing a third fluorescent emission signal by a third mean intensity, said third fluorescent emission signal being measured at a second discrete locus of a plurality of discrete loci on the second microarray, said third mean intensity being the mean intensity of the third plurality of fluorescent emission signals measured at each of the plurality of discrete loci on the second microarray, thereby calculating a third normalized fluorescent emission signal;
   normalizing a fourth fluorescent emission signal by a fourth mean intensity, said fourth fluorescent emission signal being measured at said second discrete locus, said fourth mean intensity being the mean intensity of the fourth plurality of fluorescent emission signals measured at each of the plurality of discrete loci on the second microarray, thereby calculating a fourth normalized fluorescent emission signal;
   determining a second color ratio between said third normalized fluorescent emission signal and said fourth normalized fluorescent emission signal, wherein the first color ratio and the second color ratio are determined for a same individual component of genetic matter;
   wherein said first color ratio and said second color ratio have opposite fluorophore bias:
   computing an average color ratio by averaging said first color ratio and said second color ratio, wherein the first color ratio and the second color ratio are for a pair of hybridization experiments of similar, exact replica, or identical microarrays and the same individual component of genetic matter for both members of the pair, with fluorescent label assignment reversed in one member of the pair, and wherein the averaging reduces fluorophore-specific bias in the average color ratio;

wherein said average color ratio is computed by the expression $$\tfrac{1}{2}(\log(r_{x/y})-\log(r_{x/y}^{(rev)}))$$

by said instructions for computing, wherein $r_{x/y}$ represents said first color ratio and $r_{x/y}^{(rev)}$ represents said second color ratio; and outputting the average color ratio to a user, a user interface device, a monitor, a user-accessible computer readable storage medium, or a user-accessible local or remote computer system; or displaying the average color ratio.

2. The computer program product of claim 1 wherein said first fluorophore and said second fluorophore are selected from the group consisting of Cy2-deoxynucleotide triphosphate, Cy3-deoxynucleotide triphosphate, Cy3.5-deoxynucleotide triphosphate, Cy5-deoxynucleotide triphosphate, Cy5.5-deoxynucleotide triphosphate, Cy7-deoxynucleotide triphosphate, fluorescein, lissamine, phycoerythrin, and rhodamine.

3. The computer program product of claim 1 wherein said first microarray and said second microarray are the same, the two color hybridization microarray experiment further comprising:

washing said first microarray after step (7).

4. The computer program product of claim 1 wherein said perturbed state is achieved by exposing said biological system representing said baseline state to a pharmacological agent.

5. The computer program product of claim 1 wherein said individual component of genetic matter comprises a messenger RNA, a complementary DNA, a genomic DNA, an oligonucleotide, or a gene fragment.

6. A computer program product embodied on a computer readable storage medium, the computer readable storage medium encoded with computer-executable instructions which, when executed by a processor, cause the processor to execute a method of reducing fluorophore-specific bias in gene expression data comprising:

receiving a first color ratio and a second color ratio obtained from a two color hybridization microarray experiment comprising steps (1)-(12):

(1) labeling a first pool of genetic matter, derived from a biological system representing a baseline state, with a first fluorophore to obtain a first pool of fluorophore-labeled genetic matter;

(2) labeling a second pool of genetic matter, derived from a biological system representing a perturbed state, with a second fluorophore to obtain a second pool of fluorophore-labeled genetic matter;

(3) labeling a third pool of genetic matter, derived from said biological system representing said baseline state, with said second fluorophore to obtain a third pool of fluorophore-labeled genetic matter;

(4) labeling a fourth pool of genetic matter, derived from said biological system representing said perturbed state, with said first fluorophore to obtain a fourth pool of fluorophore-labeled genetic matter;

(5) contacting said first pool of fluorophore-labeled genetic matter and said second pool of fluorophore-labeled genetic matter with a first microarray under conditions such that hybridization can occur;

(6) detecting a first fluorescent emission signal at a first discrete locus on the first microarray from said first pool of fluorophore-labeled genetic matter that becomes bound to said first microarray under said conditions;

(7) detecting a second fluorescent emission signal at said first discrete locus on the first microarray from said second pool of fluorophore-labeled genetic matter that becomes bound to said first microarray under said conditions;

(8) determining said first color ratio between said first fluorescent emission signal and said second fluorescent emission signal;

(9) contacting said third pool of fluorophore-labeled genetic matter and said fourth pool of fluorophore-labeled genetic matter with a second microarray under conditions such that hybridization can occur;

(10) detecting a third fluorescent emission signal at a second discrete locus on the second microarray from said third pool of fluorophore-labeled genetic matter that becomes bound to said second microarray under said conditions;

(11) detecting a fourth fluorescent emission signal at said second discrete locus on the second microarray from said fourth pool of fluorophore-labeled genetic matter that becomes bound to said second microarray under said conditions; and

(12) determining said second color ratio between said third fluorescent emission signal and said fourth fluorescent emission signal;

wherein:

said first microarray and said second microarray are similar to each other, exact replicas of each other, or are identical;

said first color ratio and said second color ratio are determined for a same individual component of genetic matter;

wherein said first color ratio and said second color ratio have opposite fluorophore bias; and said first fluorophore and said second fluorophore are different;

wherein the computer program mechanism further comprises computer executable instructions for:

computing an average color ratio by averaging the first color ratio and the second color ratio by the expression $$\tfrac{1}{2}(\log(r_{x/y})-\log(r_{x/y}^{(rev)}))$$

wherein $r_{x/y}$ represents said first color ratio and $r_{x/y}^{(rev)}$ represents said second color ratio, wherein the first color ratio and the second color ratio are for a pair of hybridization experiments of similar, exact replica, or identical microarrays and the same individual component of genetic matter for both members of the pair, with fluorescent label assignment reversed in one member of the pair, and the average color ratio reduces fluorophore-specific bias as compared to the first color ratio and the second color ratio; and outputting the average color ratio to a user, a user interface device, a monitor, a user-accessible computer readable storage medium, or a user-accessible local or remote computer system; or displaying the average color ratio.

7. The computer program product of claim 6 wherein said first fluorophore and said second fluorophore are selected from the group consisting of Cy2-deoxynucleotide triphosphate, Cy3-deoxynucleotide triphosphate, Cy3.5-deoxynucleotide triphosphate, Cy5-deoxynucleotide triphosphate, Cy5.5-deoxynucleotide triphosphate, Cy7-deoxynucleotide triphosphate, fluorescein, lissamine, phycoerythrin, and rhodamine.

8. The computer program product of claim 6 wherein said first microarray and said second microarray are the same, the two color hybridization microarray experiment further comprising:

washing said first microarray after said step (7).

9. The computer program product of claim 6 wherein said perturbed state is achieved by exposing said biological system representing said baseline state to a pharmacological agent.

10. The computer program product of claim 6 wherein said individual component of genetic matter comprises a messenger RNA, a complementary DNA, a genomic DNA, an oligonucleotide, or a gene fragment.

11. A method of reducing fluorophore-specific bias in gene expression data comprising:
- labeling a first pool of genetic matter, derived from a biological system representing a baseline state, with a first fluorophore to obtain a first pool of first-fluorophore-labeled genetic matter;
- labeling a second pool of genetic matter, derived from a biological system representing a perturbed state, with a second fluorophore to obtain a first pool of second-fluorophore-labeled genetic matter;
- labeling a third pool of genetic matter, derived from the biological system representing the baseline state, with the second fluorophore to obtain a second pool of second-fluorophore-labeled genetic matter;
- labeling a fourth pool of genetic matter, derived from the biological system representing the perturbed state, with the first fluorophore to obtain a second pool of first-fluorophore-labeled genetic matter;
- contacting the first pool of first-fluorophore-labeled genetic matter and the first pool of second-fluorophore-labeled genetic matter with a first microarray under conditions such that hybridization can occur;
- detecting a first plurality of first-fluorescent emission signals at each of a plurality of discrete loci on the first microarray from the first pool of first-fluorophore-labeled genetic matter that becomes bound to the first microarray under said conditions;
- detecting a first plurality of second-fluorescent emission signals at each of a plurality of discrete loci on the first microarray from the first pool of second-fluorophore-labeled genetic matter that becomes bound to the first microarray under said conditions;
- contacting the second pool of second-fluorophore-labeled genetic matter and the second pool of first-fluorophore-labeled genetic matter with a second microarray under conditions such that hybridization can occur;
- detecting a second plurality of second-fluorescent emission signals at each of a plurality of discrete loci on the second microarray from the second pool of second-fluorophore-labeled genetic matter that becomes bound to the second microarray under said conditions;
- detecting a second plurality of first-fluorescent emission signals at each of a plurality of discrete loci on the second microarray from the second pool of first-fluorophore-labeled genetic matter that becomes bound to the second microarray under said conditions;
- normalizing a first first-fluorescent emission signal by a first mean intensity, the first first-fluorescent emission signal being measured at a first discrete locus of the plurality of discrete loci on the first microarray, the first mean intensity being a mean intensity of the first plurality of first-fluorescent emission signals measured at each of the plurality of discrete loci on the first microarray, thereby calculating a first normalized first-fluorescent emission signal;
- normalizing a first second-fluorescent emission signal by a second mean intensity, the first second-fluorescent emission signal being measured at the first discrete locus, the second mean intensity being a mean intensity of the first plurality of second-fluorescent emission signals measured at each of the plurality of discrete loci on the first microarray, thereby calculating a first normalized second-fluorescent emission signal;
- determining a first color ratio between the first normalized first-fluorescent emission signal and the first normalized second-fluorescent emission signal;
- normalizing a second second-fluorescent emission signal by a third mean intensity, the second second-fluorescent emission signal being measured at a second discrete locus of the plurality of discrete loci on the second microarray, the third mean intensity being a mean intensity of the second plurality of second-fluorescent emission signals measured at each of the plurality of discrete loci on the second microarray, thereby calculating a second normalized second-fluorescent emission signal;
- normalizing a second first-fluorescent emission signal by a fourth mean intensity, the second first-fluorescent emission signal being measured at the second discrete locus, the fourth mean intensity being a mean intensity of the second plurality of second-fluorescent emission signals measured at each of the plurality of discrete loci on the second microarray, thereby calculating a second normalized first-fluorescent emission signal;
- determining a second color ratio between the second normalized second-fluorescent emission signal and the second normalized first-fluorescent emission signal;
- computing an average color ratio by averaging (i) the first color ratio between the first normalized first-fluorescent emission signal and the first normalized second-fluorescent emission signal and (ii) the second color ratio between the second normalized second-fluorescent emission signal and the second normalized first-fluorescent emission signal, wherein (i) and (ii) are for a pair of hybridization experiments of similar, exact replica, or identical microarrays and a same individual component of genetic matter for both members of the pair, with label assignment reversed in one member of the pair, and wherein the computing reduces fluorophore-specific bias for the average color ratio as compared to the first color ratio and the second color ratio; and
- outputting the average color ratio to a user, a user interface device, a monitor, a user-accessible computer readable storage medium, or a user-accessible local or remote computer system; or displaying the average color ratio;

wherein:
the first microarray and the second microarray are similar to each other, exact replicas of each other, or are identical;
the first color ratio and the second color ratio are determined for a same individual component of genetic matter;
the first color ratio and the second color ratio have opposite fluorophore bias;
the first fluorophore and the second fluorophore are different; and
the average color ratio is computed via:

$$\tfrac{1}{2}(\log(r_{x/y}) - \log(r_{x/y}^{(rev)}))$$

wherein $r_{x/y}$ represents the first color ratio and $r_{x/y}^{(rev)}$ represents the second color ratio, and wherein said normalizing, determining, computing, and outputting steps are performed on a suitably programmed computer.

* * * * *